(12) United States Patent
O et al.

(10) Patent No.: US 11,179,563 B2
(45) Date of Patent: *Nov. 23, 2021

(54) SYSTEM AND METHODS TO TRACK AND INCREASE MUSCLE EFFICIENCY

(71) Applicant: Neurological Fitness Equipment and Education LLC, Austin, TX (US)

(72) Inventors: Ki Yong O, Austin, TX (US); Garrett Salpeter, Austin, TX (US)

(73) Assignee: Neurological Fitness Equipment and Education LLC, Austin, TX (US)

( * ) Notice: Subject to any disclaimer, the term of this patent is extended or adjusted under 35 U.S.C. 154(b) by 22 days.

This patent is subject to a terminal disclaimer.

(21) Appl. No.: 16/351,358

(22) Filed: Mar. 12, 2019

(65) Prior Publication Data
US 2019/0209835 A1   Jul. 11, 2019

Related U.S. Application Data

(63) Continuation of application No. 15/247,904, filed on Aug. 25, 2016, now Pat. No. 10,232,172.
(Continued)

(51) Int. Cl.
*A61N 1/20* (2006.01)
*A61N 1/04* (2006.01)
(Continued)

(52) U.S. Cl.
CPC .............. *A61N 1/20* (2013.01); *A61B 5/0022* (2013.01); *A61B 5/02* (2013.01); *A61B 5/0205* (2013.01);
(Continued)

(58) Field of Classification Search
CPC .. A61N 1/0452; A61N 1/0476; A61N 1/0456; A61N 1/36014; A61B 5/4519
See application file for complete search history.

(56) References Cited

U.S. PATENT DOCUMENTS

| | | |
|---|---|---|
| 5,586,067 A | 12/1996 | Gross |
| 2013/0060304 A1 | 3/2013 | LaTendresse |
| 2014/0194949 A1 | 7/2014 | Wichner |

*Primary Examiner* — Paula J Stice
(74) *Attorney, Agent, or Firm* — Prol Intellectual Property Law, PLLC; H. Kenneth Prol

(57) ABSTRACT

An object of the present invention is to provide a system and method of determining muscle efficiency and inefficiency in a patient or subject and being able to quantitatively determine measurements that communicate between practitioners the condition, the health, and the efficiency state of any muscle. The efficiency of a muscle is defined by the ability of the brain to bridge a proper communication to the muscle by sending normal action potentials; the bridge is often compromised during injury, improper training, or from poor habits of bodily movement. The standardization of these efficiencies allows for the isolation of particular areas of the muscles that are inefficient and efficient. Further, with varied application of electrical pulses, a bridge that mimics the natural action potential is provided and can enhance muscle efficiency in a way that achieves higher levels of success in bodily healing and physical training than in any prior art. The current invention uses multiple, select sets of electrical currents at sound wave frequencies with specific forms of movements. The application of electrical currents can also be synchronized with extensions and contractions of muscles to stimulate the expedited bridging of brain to muscle and increase the efficiency of muscles. The current invention discloses a system to deliver these electrical currents and offers the capabilities to standardize these techniques to reconnect the brain to these muscles to an efficient level.

20 Claims, 15 Drawing Sheets

Related U.S. Application Data

(60) Provisional application No. 62/209,863, filed on Aug. 25, 2015.

(51) Int. Cl.

| | | |
|---|---|---|
| *A61N 1/02* | (2006.01) | |
| *A61N 1/36* | (2006.01) | |
| *A61B 5/00* | (2006.01) | |
| *A61B 5/0533* | (2021.01) | |
| *G16H 10/60* | (2018.01) | |
| *A61B 5/08* | (2006.01) | |
| *G16H 20/30* | (2018.01) | |
| *A61B 5/024* | (2006.01) | |
| *A61B 5/145* | (2006.01) | |
| *A61B 5/02* | (2006.01) | |
| *A61B 5/1495* | (2006.01) | |
| *A61B 5/0205* | (2006.01) | |
| *A61B 5/021* | (2006.01) | |
| *A61B 5/24* | (2021.01) | |

(52) U.S. Cl.
CPC ........ *A61B 5/02405* (2013.01); *A61B 5/0533* (2013.01); *A61B 5/08* (2013.01); *A61B 5/1495* (2013.01); *A61B 5/14542* (2013.01); *A61B 5/4519* (2013.01); *A61B 5/4836* (2013.01); *A61B 5/6824* (2013.01); *A61B 5/6828* (2013.01); *A61B 5/7257* (2013.01); *A61N 1/025* (2013.01); *A61N 1/0452* (2013.01); *A61N 1/0476* (2013.01); *A61N 1/205* (2013.01); *A61N 1/36003* (2013.01); *A61N 1/36014* (2013.01); *A61N 1/36034* (2017.08); *G16H 10/60* (2018.01); *G16H 20/30* (2018.01); *A61B 5/021* (2013.01); *A61B 5/0816* (2013.01); *A61B 5/24* (2021.01); *A61B 5/4824* (2013.01); *A61B 2503/10* (2013.01); *A61B 2562/046* (2013.01)

30 Seconds

Frequency Change During Squat

30 Seconds

Frequency Change During Squat

SYSTEM AND METHODS TO TRACK AND INCREASE MUSCLE EFFICIENCY This application is a continuation of prior application Ser. No. 15/247,904, entitled "System and Methods to Track and Increase Muscle Efficiency," filed on Aug. 25, 2016, which claims priority of U.S. Provisional Application No. 62/209,863, filed on Aug. 25, 2015, the disclosures of which are hereby expressly incorporated by reference in their entirety.

TECHNICAL FIELD OF THE INVENTION

The invention relates to the use of multiple sets of electrical waves having sound wave frequencies that allows one set of waves to sync with the body and at least one other set of pulsed sound waves to harmonize with and stimulate the nervous system in a manner that, when combined with specific forms of exercises, leads to recognition of efficiency in that muscle and ways to standardize the measurement of muscle efficiency and to increase muscle efficiency in those selected muscles. By creating parameters for measuring efficiency in muscles, a system is derived that allows users to determine muscle efficiency and track improvements in muscle efficiency during treatments. The treatments are designed to bridge communication between the brain, nervous system, and muscles by mimicking the natural action potentials of the human nervous system. Many unexpected derivative methods of building muscle efficiency and systems that are used in conjunction are described below.

BACKGROUND OF THE INVENTION

Despite modern advances in medicine and medical equipment, sophisticated techniques to accelerate the basic biological processes of healing and training are only now being discovered. In the fields of training and healing muscles, using a few particular movements combined with electrical stimulation is well known, but the current invention uses two or three specific electrical direct currents using sound wave frequencies to mimic voltage waveform patterns of an action potential. When done with a very particular set of bodily movements, the bridging of communication between the brain and muscles allow the muscles to increase their efficiency, which results in accelerated results in healing and training that have surprising statistical significance. What is more unexpected is that the inventors have been able to quantify this inefficiency in muscles based on data from the use of these electrical currents and precise movements of the body that allows a new way of studying physiology and categorizing muscle healing and development.

Introduction

The human body has evolved to react to different environmental conditions in an efficient manner. A scrape on the arm immediately triggers the body to address the wound by coagulating the blood and initiating the white blood cell response. A developing athlete with a new interest in basketball quickly builds a connection between the complicated neuronal instructions and a diverse set of muscles that constantly adjusts when the athlete is learning new skills or growing stronger.

Science has advanced medicine and immunology in many ways, but overconfidence in modern techniques has in many ways deterred research in processes that involve natural, biological ways of healing and growing. Let's take the example of a knee injury. A common knee sprain may involve the swelling and inflammation in and around the knee's major ligaments. This knee injury also triggers a response in which the body changes output to the muscles around that knee. This response actually weakens the leg, because the inability to contract or release these muscles reduces the functional ability of that leg. In particular, there is a reduction in that leg's ability to absorb force. The muscles such as the hamstrings, quads, and calves around the knees become less able to support the joint, permitting more force to be placed back on the injured joints and ligaments and actually increasing the risk of re-injury. These muscles are reduced in efficiency because of changes in function of the controlling aspects of the brain and nervous system, which begin to provide fewer stabilizing pulses to these muscles. These pulses are well known in the science community as "action potentials."

Historically, this simple concept is misunderstood. Because of injuries to the cells in damaged areas, many researchers have mislabeled the problem as cellular disruptions. There is no empirical evidence that eruption of cells directly cause the lack of efficiency in these muscles. Because the lack of efficiency in muscles results from lack of use as well, even non-injured muscles that are misused or unequally used also show the same type of muscular inefficiency. And while some researchers believe that the reversal of polarity in the cells directly results in the lack of muscle contractions or ability to effectively contract, there is no empirical evidence that polarity in an injury has any significance to the science behind the lack of efficiency in muscles. Thus, all that is known is that these muscles are reduced in efficiency.

The body depends on muscles to absorb force in most movements, but injuries, such as knee injuries, impair this ability by reducing the efficiency of these muscles. Even when there is actually no damage to the surrounding muscles, these muscles are reduced in efficiency as the injury causes the body to change the pattern of using these muscles. Evolutionarily, this makes sense, because this signals the body to not use the leg while we address the injury. However, it is a problem when these inefficiencies persist even after the injury is healed. Modern techniques typically set the knee or cast it in an attempt to protect a damaged area, but immobilizing the knee further reduces the efficiency of the whole leg's recovery.

This disclosure does not purport to invent the use of electrical currents to stimulate muscles. Even the use of multiple electrical frequencies is well known in the industry and the use is in the public domain. For example, apparatuses in U.S. Pat. No. 4,374,524 to Hudek (1983) illustrates the use of a square-wave signal generator in conjunction with a plurality of phase-locked loops and low-pass filters to produce a plurality of sine-wave, primary signals that can be used to activate muscles. U.S. Pat. No. 4,071,033 to Nawracaj et al. (1978), and U.S. Pat. No. 4,153,061 to Nemec (1979) teach two primary signals of different frequencies and that also modulates amplitudes in primary signals to achieve various therapeutic effects.

The use of direct current on the muscles, which is not well studied (because of historical difficulty of penetrating the outer skin to reach inner muscles using direct current), and using wave patterns that resemble exponential waves is disclosed in U.S. Pat. Nos. 5,107,835 and 5,109,848, which was published in 1992. These wave patterns purport to allow the highest levels of direct current to penetrate into the body, by using specific pulses wherein there exists one electrical waveform with a set of sound wave frequencies overlaid with another electrical waveform with a pulsed set of sound wave frequencies wherein the pulsed set of sound waves results in the treatment of muscles. In the end, the pulses are only designed to send pulses to the body. Although conventional A/C powered muscle stimulating devices trigger the action potential of a nerve, it does so by overpowering the ion channels that produce the action potential. There has never been an ability to provide (in-vivo) an electrical current that mimics an actual action potential so closely that the body responds to it as if it was a real action potential. Up until now, there has never been a way to measure if this was even possible.

In U.S. Pat. No. 5,107,835, the inventor uses what they call a "periodic double exponential" wave pattern that relies on the use of multiple frequencies and the use of wave shapes that are exponential. Although this pattern of exponential characteristics has been proven clinically to address certain neuronal responses to muscles, the basis for which the inventors of the U.S. Pat. No. 5,107,835 patent relies on it working is without supportive data.

U.S. Pat. No. 5,107,835 patent is described as "the substantially constant amplitude periodic-exponential portion of the sum signal that is applied to a patient's body by the apparatus" shows the shape of this exponential wave characteristics. A reproduction of the prior art wave signal is shown in FIG. 1. In particular, FIG. 1 shows the wave pattern 82 that is the basis of U.S. Pat. No. 5,107,835. It uses electrical waves and in baseline slope 102, there is no steady flat baseline; instead, the baseline is shown to be downward in slope. Downward slope 102 is also named baseline 102. In baseline 102, there is no lower waveform signal that would represent a refractory period, or a downward shape. If one existed, it would have the dotted line appearance in 103. There is a repeated pattern for sure, but because there is no flat baseline or a refractory period downward bell shape of the wave in direct current, it lacks the type of shape that exists in nature, which is namely the shape of an action potential. Studies have shown that without reproducing the action potential waveform, the body may not fully respond to it as if it were a real action potential.

Thus, this wave pattern is not like the actual wave pattern of electrical voltage current experienced by the nerves. All cells in animal body tissues are electrically polarized—in other words, they maintain a voltage difference across the cell's plasma membrane, known as the membrane potential. This electrical polarization results from a complex interplay between protein structures embedded in the membrane called ion pumps and ion channels. In neurons, the types of ion channels in the membrane usually vary across different parts of the cell, giving the dendrites, axon, and cell body different electrical properties. As a result, some parts of the membrane of a neuron may be excitable (capable of generating action potentials), whereas others are not. Recent studies have shown that the most excitable part of a neuron is the part after the axon hillock (the point where the axon leaves the cell body), which is called the initial segment, but the axon and cell body are also excitable in most cases.

Each excitable patch of membrane has two important levels of membrane potential: the resting potential, which is the value the membrane potential maintains as long as nothing perturbs the cell, and a higher value called the threshold potential. At the axon hillock of a typical neuron, the resting potential is around −70 millivolts (mV) and the threshold potential is around −55 mV. Synaptic inputs to a neuron cause the membrane to depolarize or hyperpolarize; that is, they cause the membrane potential to rise or fall. Action potentials are triggered when enough depolarization accumulates to bring the membrane potential up to threshold. When an action potential is triggered, the membrane potential abruptly shoots upward, often reaching as high as +100 mV, then just as abruptly shoots back downward, often ending below the resting level, where it remains for some period of time. This depression below the initial level is known as the refractory period, during which the membrane's ions reorient themselves to once again establish the resting potential. The shape of the action potential is stereotyped; that is, the rise and fall usually have approximately the same amplitude and time course for all action potentials in a given cell. In most neurons, the entire process takes place in about a thousandth of a second. Many types of neurons emit action potentials constantly at rates of up to 10-100 per second; some types, however, are much quieter, and may go for minutes or longer without emitting any action potentials.

FIG. 2 shows an action potential that is well studied and is considered prior art for purposes of this disclosure, but the particular action potential in FIG. 2 is of an electrical voltage level over time of an action potential in a human. This voltage wave pattern is not known to be the model of any electrical current stimulation muscle device using direct current to sync with the nerve and therefore, the current invention involves models based on this waveform. There are many ways to describe the scientific shape of a waveform. Depending on the type of specificity needed, these waveforms can have very specific names, but for purposes of understanding what the shape of an action potential is and what the shape of current prior art electrical current machines provide, only simple terms are needed. FIGS. 3A-3F show various waveform shapes. In one general view, these can be considered the essential "six types of waveforms" or "wave pattern shapes." As shown by the U.S. Pat. Nos. 5,107,835 and 5,109,848 pattern, the waveform pattern they have decided to use is an "exponentially decaying" which is similar to the classic waveform of FIG. 3F. As shown by FIGS. 4A-4C, the known uses of direct current electrical current is currently in the exponentially decaying waveform as shown in prior art FIG. 5, which is the waveform of the initial peak and immediate voltage of the waveform used to create a stimulus in prior art machines dating farther back than 1992. See U.S. Pat. Nos. 5,107,835 and 5,109,848, e.g. As shown in the downward slope 501, the slope is in the shape of FIG. 3F, which is classically known as an exponential decaying waveform. The exponential decaying waveform is followed by a section that is considered to be the baseline 502, but unlike the action potentials of natural animals, there is no flat horizontal line, but rather a slow slope downwards. The distinction is significant because it allows the body to have a state of equal balance which is a flat horizontal line, wherein the next action potential can initiate, which is described in detail below.

But as shown in its disclosure, the pattern of waveform shape goes drastically upwards in the next stage of a classic 1992 machine that stimulates the body using direct current. As shown in FIG. 6, the next stage of the prior art waveform usage uses a next peak 601 in the voltage reading but has a sharp left turn 602.

In contrast, the downward slope of the waveform in the real action potential has more uniform downward shape as shown below in sections 701 and 702 where even though it is a sharp decline, there are no near right turns or 90 degree turns as shown in section 602 above. Even in sections 703, there is a baseline formation that does not exist in the FIG. 6 corresponding representation. Furthermore, FIG. 8 shows a standard "S" shape exponential rising to a peak wavelength form, and once again, there are no abruption angle changes that exits in section 602 of FIG. 6, which is a 1992 prior art voltage meter reading of a direct current for the stimulation of muscles. FIG. 8 shows the next natural rising section of a natural action potential. Section 801 does show a smooth S formation wavelength, but section 802 shows a leveling off section.

The leveling off sections of the natural action potentials are noted, because they are clear distinctions from other uses of direct current treatments of muscles. The reason why there was a movement away from the use of a wavelength that mimics the more natural action potential shape is because of the previous misunderstood science.

Previously, the reasons for the force of stress being placed on ligaments and joint tissues instead of muscles was believed to be because of a polarity creation in the injury. Because they were characterized as having cellular disruption sites wherein there was a breakdown in the polarized nature of these cells. In most cases, this misunderstanding has hindered advancement in this field. Because the understanding that such direct current waves are needed to trigger these stimulations, it was assumed that the polarized nature of the sites after treatment healed the cellular disruption sites. This is a misunderstanding.

What is understood is this: injuries lead to alterations in the usual function of muscles, making them inefficient. Because not all muscles become inefficient, there is a physiological different between muscles that are inefficient and those that are efficient. When those two can be compared in an individual, a ratio of efficiency in muscles can be measured. When present, this inefficiency is due to the brain's reduced ability to engage in the proper connection to the muscles. The muscles are generally controlled by action potentials, transmitted by the brain through the nervous system, that have a very specific shape. A further characterization of these waveforms that mimic the waveform of an action potential differentiates from the 1992 use of direct current which was only designed to create pulses.

The use of direct current waveforms using electrical currents in two or more sound wave frequencies can produce a natural action potential formation. When this combination of wave forms is used to penetrate the skin and fats to reach the nerves, the result is a surprising enhancement of muscle efficiency.

In addition, the waveform shape shows a patterned exponential rising shape that is uniform as shown in FIG. 8. The S shape of the exponentially rising curve has a leveling peak area at 802. There are no abrupt changes.

As shown in FIG. 2A of U.S. Pat. No. 5,107,835, the waveforms are akin to exponential decaying shapes and also are not similar to actual action potential voltage wave shapes. The real action potential has the purpose of creating an efficient means to send a message down to various specific muscles in as fast and as controlled a manner as possible. In doing so, there is a baseline by which a specific shaped action potential voltage is sent down the nerve. Because of this specific shape, current science understands that the brain actually receives feedback from these action potentials. Imagine a boomerang: using alternating current or even pulses of direct current to activate the action potential does the job of contracting the muscle and telling the brain that the muscle is contracted. That is equal to the throwing of the boomerang. What is needed and contemplated in this invention is the ability to use or mimic natural action potential signals which scientifically has been shown to provide feedback to the brain that the firing of the action potentials has actually taken place. Then, it will believe that movement is being reported from the relevant muscles and will respond to either "protect against" or allow that movement. This response gives insight into the efficiency of that muscle. There is no mistaking what the action potential shape is used for and the body recognizes the natural form. Furthermore, the specific use to alter specific forms of waves has not been studied in the use for increasing the efficiency of muscles.

When the brain recognizes the natural form, it then has the ability to resync and re-engage that muscle, which by definition makes the muscles more efficient. When the firing of the action potential is matched with the nerves in a way that the brain believes that it is the real action potential, the feedback is akin to the matching of a thrown boomerang so that the thrower can catch it and does catch it. In other words, the brain receives the signal as if the muscle had been working on its own, and, in turn, learns to adopt this new, more appropriate way of using the muscles that it has been shown.

What is needed is a way to utilize the human body's naturally-evolved, biological processes for healing and strengthening, using modern technology not to outsmart the body, but rather to accelerate these natural processes by allowing the body to heal injury or enhance the function of the addressed muscles.

SUMMARY OF THE INVENTION

Although prior art methods have shown the use of electrical current, there are currently no methods that mimic the shapes of the waveforms that exist in the human and animal bodies in a manner that penetrates to the nerves. And there are no disclosed methods of fully using these biological conditions to help accelerate muscle efficiency or communicating within a community a reliable standard that can relay general muscle efficiency in one person to another.

Initially, it is the object of the invention to derive a completely different measurement for a qualitative measurement of muscle efficiency/inefficiency and a quantitative measurement of muscle efficiency/inefficiency and muscle state and progress. Because there has never been an ability to quantify muscle inefficiency, there had been no efforts to quantitatively describe parameters that chart the current efficiency state of a muscle and the ability to communicate between people the status of the efficiency of the muscle and its health or fitness. It is an object of the invention to be able to measure the progress of muscle efficiency in order to study statistical measurements of various treatments using multiple sound frequencies of electrical waves that bridge neuromuscular communications so that measurements and studies can be conducted in laboratory and clinical settings. It is an object of the invention, therefore, to provide a system and methods that results in the ability to use multiple electrical waves in sound frequencies that have the waveform that is more similar to the action potential of the nervous system. A further invention is the ability to use multiple frequencies in sound waves to create an additional nervous feedback response to the brain so that the brain responds to it as it would to a natural action potential. A further invention is the ability to change the frequency of the actual waveforms and match it with frequencies of the actual action potential the body would normally feel if the muscle was healthy, and to increase the power of that matching frequency in accelerated pathways such that during certain exercise movements, there is a discernible match of the reproduced action potentials and natural action potentials. The coordinated specific muscle movements with the invention disclosed further enhances the rebridging of the brain's connection to these muscles that allows a much higher rate of improving muscle efficiency, which leads to accelerated results in healing and training. A further invention is the ability to use various forms of currents that are timed, coordinated with various forms of exercises that are directed to engage the bridge between the brain and the efficient use of muscles in accelerated forms. A further invention involves the use of the standardized models of objective tests to get results from subjects that are unable to express different degrees of discomfort, the subjects include animals, infants, and people unable to communicate, such as comatose people. A further invention is the specific application of these currents that allows for the extension of muscles to support higher levels of muscle efficiency leading to higher performance and faster results in training.

BRIEF DESCRIPTION OF THE DRAWINGS

For a more complete understanding of the present invention, and the advantages thereof, reference is now made to the following descriptions taken in conjunction with the accompanying drawings, in which.

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Introduction

Preferred embodiments of the present invention are directed toward a method of using multiple, direct electrical currents to mimic the action potential of a nerve by first using at least one set of direct current electrical currents in the range of sound frequencies to synchronize the frequency and voltage with the body and then providing another one or two set of direct currents that are in the wave shape of an action potential either in direct mV measurements or in a similar waveform pattern depending on the individual or subject, and then creating a baseline from the measurement of either the changes in heart rate, breathing rate, blood pressure, blood oxygen saturation, galvanic skin responses, or pain/discomfort levels which allows for the creation of an efficiency standard for which a muscle can be measured for efficiency.

Further, embodiments of the current invention use the reproduced action potentials in a frequency that would match the natural body's changing frequency in stationary positions or during specific exercises that enhance the bridge between the brain and "inefficient" muscle.

In accordance with preferred embodiments of the current disclosed system and methods, there is provided a method of delivering specific electrical currents having waveforms that more closely approximate the shape of the action potential of the human and animal nervous system. Sound that is perceptible by humans has frequencies from about 20 Hz to 20,000 Hz. With various electrodes placed on specific muscles and the distribution of multiple electrical waves with sound wave frequencies, the use of a first sound wave syncs, or harmonizes with parts of the body, such as the water and fats and epidermis, to reduce the impedance or resistance of those tissues. The use of a second sound wave is performed in pulses that reaches and stimulates the nervous system and allows the brain to recognize the natural, more efficient usage of the muscle as its natural state. In doing so, these pulses bridge the brain's control of the muscles, re-establishing a connection that allows for more efficient usage of these muscles. By performing specific training exercises and specific movements, it is possible to accelerate the bridging process to re-engage the body's muscles more efficiently. A third sound wave can be used to create the dip or other parts of the action potential when synchronized with the second sound wave electrical current, it can (also??) produce the mirror image of an action potential.

Figure 9:
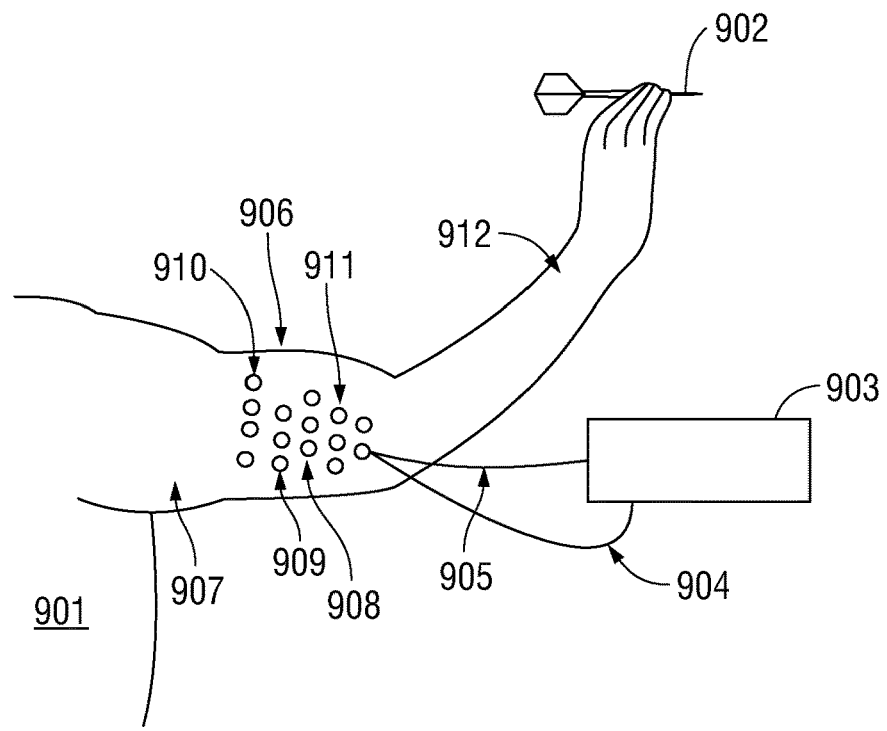
FIG. 9 shows another embodiment of the current system wherein muscle efficiency/inefficiency can be measured and treated.

In accordance with embodiments of the current invention, FIG. 9 shows how electrodes and movements can be combined towards achieving a muscle efficiency standard or better improving the muscle efficiency by showing an individual 901 throwing a dart 902 with the arm 912 almost in the extended position. In other words, if this arm 912 was in motion, the picture in FIG. 9 shows an arm that is almost at the release of the dart 902. In this particular example, there is a biceps 906 and a triceps 907. The understanding that these are antagonist muscles is essential in showing muscle efficiency. Because there typically is discomfort associated with the delivery of the multiple electrical currents wherein at least one current harmonizes with the body using sound wave frequencies and a pulsed frequency that mimics a natural action potential, the level of discomfort experienced can be used to help quantify the degree of muscular inefficiency.

These action potentials can be individualized so that they perform on various animals. Although nature respects the waveform of the action potential, obvious differences between humans and animals allow us to recreate the differences in these second frequency to match the animal in particular. The closer the match between the wave form and the organism's innate action potential, the higher the success of rebridging the gap between the brain and muscle. In FIG. 9, system 903 delivers that multiple frequencies of direct current through electrodes 904 and 905. The multiple frequencies allow one set to harmonize with the body (which can be conceived as penetrating the outside body and organs) and another set to mimic that action potential of a healthy or even highly active nerve. This electrical current can be applied to different areas of the muscles, and in this example there are many electrodes at 907, 908, 909, 910, and 911.

There are a number of ways to calculate the inefficiency of muscles. Again, the inefficiency of muscles for purposes of this patent is defined as a reduced ability of the brain to connect with the designated muscle, resulting in a deficiency in the ability to normally send an action potential to the muscle. The inefficiency can be measured in many ways, but there is a preferred way. Table 2 shows the different ways that the inefficiency standard can be measured. (Currently, there are no other known ways to measure the inability of the brain to associate with muscles in a standardized way that reflects the inefficiency of its normal action potential).

A. Qualitative Muscle Function and Performance

Muscle extension, known as eccentric contraction, is vital for efficient movement in most settings—particularly for high levels of athletic performance and fitness, and also for many movements of daily life. Modern research shows clearly that proper muscle efficiency allows for eccentric muscle contractions to absorb the forces encountered during bodily movement, thus protecting more passive bodily structures from having to handle that force. When force is not properly handled by the muscles, the body has to rely on the secondary, passive supports of ligaments, bone, and other connective tissues. These structures are sensitive to mechanical perturbations. They can become damaged, or can even respond by alerting the body to the possibility of damage. This signal causes the body to change its use of muscles in the area, which can reduce muscle responsiveness and efficiency, impair performance, and increase the risk of injuries in subsequent activities.

Unlike the U.S. Pat. No. 5,107,835, the current usage of these frequencies can become individualized and specialized based on the particular movement which unexpectedly heightens the efficiency of these techniques that that were well known in the industry to contract muscles. Although U.S. Pat. No. 5,107,835 got much of the science wrong, the current invention relates in that the proper distribution of proper electrical waves with sound wave frequencies results in a faster restoration of muscle efficiency. The current research focuses on the true nature of these interactions, and the results show that their reactivation is not due to them contracting the muscles or re-triggering the muscles back to a state of full recovery, but more that these pulsed currents properly trigger neuronal feedback that allows the bridging of the brain's own control of these muscles.

Clinical evidence now shows that there are more effective means by which these various electrical waves with sound wave frequencies can be used in treatments or training sessions. In the first embodiment of the current invention, there is a method of increasing the efficiency of muscles comprising the application of a first and second of electrical currents to a muscle wherein the first and second electrical currents are direct currents in the frequency of sound waves between 20 hz and 20,000 hz and where higher levels of muscle efficiency is achieved. U.S. Pat. No. 5,107,835 discloses a similar type of machine where there is an application of multiple electrical currents for the stimulation of the muscles, but the current invention relates to the proper means by which to use such a device to actually increase the efficiency of muscles. To do so, there must be specific application of proper electrodes to particular set of muscles and a way of creating a baseline so that muscle efficiencies can be measured.

For example, in performing a squat movement, the quadriceps muscles have to lengthen to absorb force and keep that force out of the knee and hip joints. Placing electrodes on the vastus medialis and vastus lateralis, and applying a signal of appropriate frequency and power, can facilitate those muscles' ability to eccentrically contract, resulting in a more efficient squatting movement. In addition to helping to protect against injury, this approach can also prepare the quadriceps muscles to contract more powerfully in the second half of the movement (moving up from the bottom of the squat), which leads to greater strength and speed of movement.

In a simplified look at the action of throwing a dart, the main action is that of elbow extension. The triceps muscles provide the major impulse for this action, while the biceps muscles provide a force in the opposite direction that could resist the elbow extension. In order for the extension to happen smoothly, the biceps must lengthen, or eccentrically contract, at the same time and at the same velocity as the triceps shortens. If the bicep were to resist, it could interrupt this movement, which could reduce the smoothness and precision of the movement, cause force to transfer into the elbow joint and increase the risk of injury, or stop the movement altogether. It would also cause energy to be wasted in the process, as the triceps have to exert extra energy to overcome the resistance of the biceps. The electrical signal can be used to stimulate the biceps to lengthen, so that they do not resist this movement.

Figure 14:
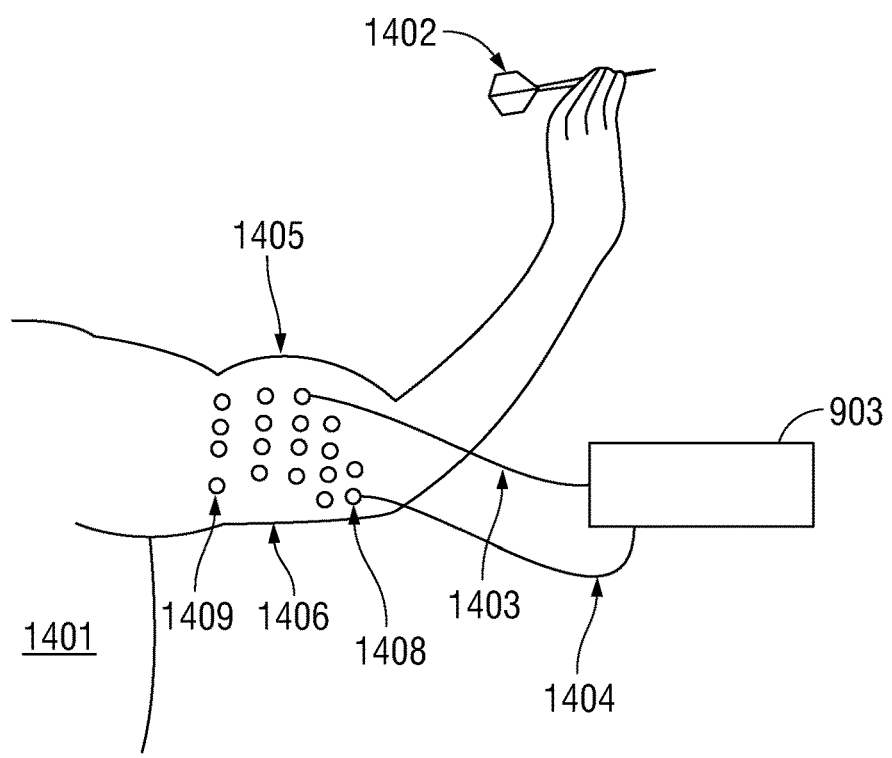
FIG. 14 shows the physiological form of a contracted bicep during the initial motion of throwing a dart which provides the setting for embodiments of the current invention.

This process is exemplified in FIG. 14 which shows the contracted position of the arm prior to throwing of the dart. Electrodes exemplified by 1408 and 1409 show the different possible areas of precise placements in the throwing of dart 1402.

The first and second electrical currents are applied to the muscle with a predetermined level of power and direction of negative and positive polarity individually of the first and second electrical currents. In cases where the brain is ineffectively stimulating a muscle, the current invention calls this "reduced muscle efficiency" or "muscle inefficiency." For example, muscles can be grouped into agonist and antagonist muscles. If the quads are the dominant muscles, then the underside hamstrings are its opposing non-dominant muscles. In many people, the lessened use of hamstrings over time results in the brain not having a bridge to connect to the hamstring. The comparison of the dominant muscle and the non-dominant muscle efficiency can be made in accordance to criteria in Table 2.

Although the application of these electrical waves of sound wave frequencies produce pulsed contractions with the muscles, the power at which the electrical waves are provided can produce stronger contractions in less efficient muscles. The stronger the contraction, the less efficient the muscle is, or in other words, the less it is bridged to the brain and the less it can be effectively stimulated to work to absorb force and protect the body's joints. During training of agonist muscles, the bridge to the antagonist muscles (if it is not trained as well) will by comparison be smaller. In injuries, the effects on muscles surrounding the injury result in inefficient connection to the brain. The level of efficiency may also vary by individual (by their weight, age, gender, hydration level, training status, and many other factors). But what is consistent is that one individual tends to maintain the same level of efficiency, and thus one individual's progress can be measured by comparing data from different dates.

Example 1

There is a threshold of power which all humans can achieve before complete immobilization. If that number is set at 100, we can call it the Maximum Threshold Level ("MTL"). There is also a maximum level of discomfort felt by an individual, and that number can also be designated for each individual and set depending on the particular client. For example, if Client A is given the electrical sound wave currents progressing from ° to higher power, the level at which the Client A states "STOP" or if there is conventional device for Client A to stop the process when maximum pain is felt (e.g., conventional stop buttons known in treadmills is used) that number can be expressed as Maximum Pain Level ("MPL"). Each patient can have a ratio of MPL/MTL at a diagnostic phase of Client A. Thus, on subsequent visits, this MPL/MTL can be compared. If Client A stops the process of power at 20, Client A will have an MPL/MTL ratio of 20/100 or 0.2. On subsequent visits, if Client A is able to achieve 40, than his ratio increases to 40/100 or 0.4. The MTL would be different in each individual for this particular embodiment because the MTL would be set during an initial diagnostic testing of Client A.

If a ratio is needed that tests against a standard, there can be incorporated two other variables. MMTL is the Maximum Machine Threshold Level, wherein ratios can be made and compared to a constant that allows comparisons of different individuals to an absolute scale. Tracking progress of each individual by comparing his thresholds with statistical data when compared to a maximum machine level allows for the tracking of statistical variations of different individuals and tracking their muscle efficiency by grouping other factors, like weight, age, gender, height, hydration level.

Another variable includes the Minimum Inefficiency Level ("MIL), which is the level at which Client A notices the inefficient bridging between the brain and the muscles. This can manifest as subjective discomfort, a feeling of tension as if one has to "fight against" the machine, or being visibly shifted or moved out of position by protective muscular contractions. By using MIL with other variables like MMTL and MPL and MTL, various statistical ratios can be created for the use of statistical studies that are quantitative. At best, prior art has only tried to qualitatively measure "cellular disruptions."

In one of the embodiments of the current invention, what is disclosed is a way to measure muscle inefficiency wherein "muscle inefficiency" is defined by the reduced ability of the brain to bridge electrical communications to particular muscles that allows the muscles to properly contract and relax. In other words, there is disclosed a measure, or score, or a quantitative, unit-based system wherein one person can communicate the physiological efficiency of a muscle to another person and where the other person would have a quantitative understanding of the muscle condition and its efficiency. In doing so, such measurements can lead to a quantitative understanding of the progress during or throughout different treatment periods.

By using different parameters, a study of the disclosed electrical currents can provide an accurate score of muscle efficiency. This can be called a Neuroscore. A Neuroscore can let people know what level of efficiency a particular muscle has, much like the blood pressure is a quantitative measurement of pressure exerted by circulating blood upon the walls of blood vessels which is expressed in terms of the systolic (maximum) pressure over diastolic (minimum) pressure and is measured in millimeters of mercury (mm Hg). Norms of healthy and unhealthy blood pressure are well understood in the medical community. With the present invention, norms of elite, average, and poor muscle efficiency can be similarly understood within the medical, physical therapy, sports training, and similar communities. The Neuroscore is a measurement of muscle inefficiency. In one embodiment, the Neuroscore is measured by [MPL]×[frequency]×[power]×amplitude×Y where Y is the average heart rate or heart rate variability over a certain time period, such as one minute.

In another embodiment the Neuroscore is measured by using average heart rate or heart rate variability over 1 minute+the number of breaths in 1 minute while on a certain level of the machine. The certain level can be the MPL or MMTL or MIL. Such Neuroscore can be scaled from a 0 to 3 scale using conventional ratios. Such Neuroscore can alternatively be scaled to a 0 to 100 unitary measurement system having proportional measurements.

Figure 16:
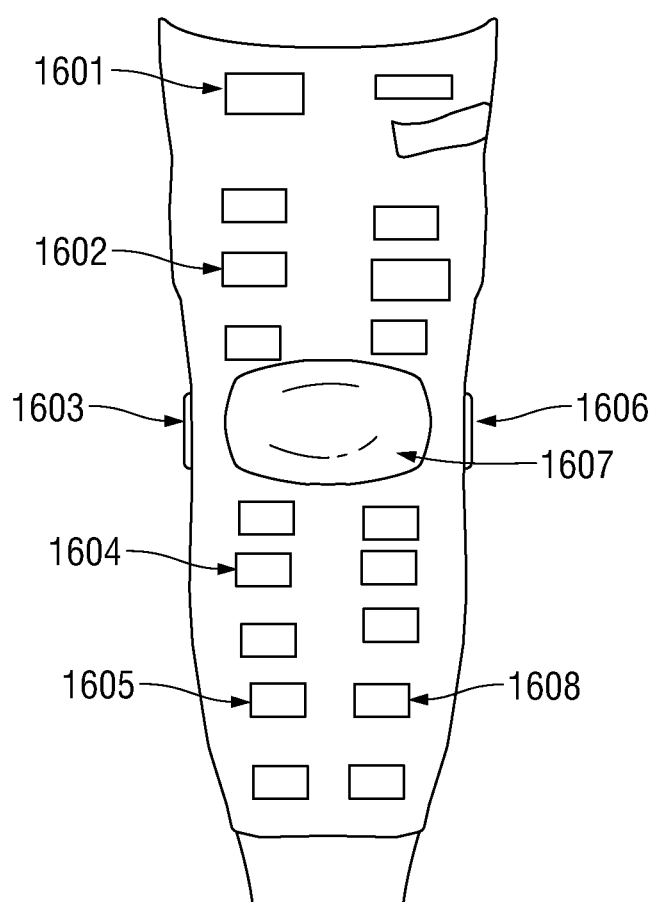
FIG. 16 shows a leg wrap and electrode system in accordance with another embodiment of the current invention.

The specific location of the electrode placement can be stored by using conventional grids. For example, the quads of the leg can be broken down into an XY coordinates axis as in FIG. 16, and by doing so, there can be a specific location description of the electrode's placement. By doing so, another factor of specific electrode placement can be used in the factor of a Neuroscore. For example, the difference in heart rate over a minute period of time having the electrode in A1 position as opposed to a D4 position would map muscle inefficiency individually for the different locations. Heart rate is simply an objective measurement of exertion by the subject. So when the electrical currents run through an area where the muscles are inefficient, the subject experiences more exertion because the lack of communication between the brain and muscle causes the protective responses with associated discomfort experienced by the patient. These responses are neurological, and will also affect other aspects of the body that are neurologically controlled, like heart rate. Over a certain period of time, Client A can be measured in heart rate or heart rate variability while the electrodes are placed in one area or another. This provides a quantitative basis by which a Neuroscore can provide a score showing muscle inefficiency.

The Neuroscore of each muscle may be different, because the level of amplitude and frequency that is needed to stimulate an efficiency response will likely be different in each muscle. In other words, when the Neuroscore is calculated for the quads and hamstrings, each may have a different baseline of electrical current parameters. Thus, each muscle may have a different Neuroscore. In one embodiment, Client A can say that his Quad Neuroscore is 45.5 and his Pectoral Neuroscore is 50. Each of these Neuroscores will be based on its own respective criteria including heart rate or other objective physiological measurement, MPL or MMTL or MIL, and whatever factors best enable the formula to measure muscle efficiency.

One of the best benefits from a score system is the ability to track progress or track parameters for statistical studies on success. Success can be measured by the change of inefficient muscles to levels of greater efficiency. That change can be quantified as the delta in Neuroscore over a certain time period. Studies have shown that types of algorithms needed for each and every muscle is different. For example, the Quads can produce a variety of heart rate from 90 to 160 in a 40 year old male, but the variation of heart rate for that same 40 year old male in the calves is 85 to 130. The differences are mostly due to the size of the muscle and the density of nerve concentration. Muscles that require greater precision for finer movement have a higher density of nerves for greater control, whereas muscles that perform more gross movement have fewer nerves. The same machine output can deliver a differing amount of current because of the density of nerve concentration. Also, stimulating a larger muscle will create a greater demand for energy than a smaller muscle, and will tend to have a larger effect on heart rate. Thus, the formula can compensate by allowing a different method of Neuroscore calculation for the Quads and a different one for the Calves, each having a different formula incorporating different ranges of heart rate. Other factors like MPL, MMTL, or MIL are also different for each muscle group. The current invention, however, uses a novel form of these parameters in measuring muscle efficiency.

In an embodiment of the current invention, there is conceived a conventional microprocessor, memory, input means, export means, output device (like a screen) and power source to store individual client levels of information including gender, weight, height, age, body fat, heart rate, and other physical parameters. It also allows for the processing of MPL and MTL information, its ratio and other ratios. There is also a LFS ("LEVEL OF FIRST SENSATION") that can be used as a factor. Such ratios can be used to build a chart of progress or even graphs of progress to Client A. Such information can be studied as to what links can be made between various health parameters and muscle efficiency.

Client level information and ratios stored in the client information data can be changed or progressively tracked using conventional ways to database client information, not excluding conventional database SQL techniques. Client information can be compared in past methods wherein further progress is stored and new ratios of levels of maximum levels of discomfort is compared to baseline.

The use of this invention's particular ability to individualize the frequency of the reproduced action potential allows the rebridging of the brain to inefficient muscles by mimicking the actual neuron action potential. This heightens the level of "awareness" the brain has of these areas of inefficiency, and when combined with exercises that contract these muscles, the bridge to the brain is reconnected much faster. In many case, there is 20-50% improvement in efficiency just in the first application of the device. In over 500 patients that were applied this wave with movement techniques that coincided with the contraction of that muscle, there was immediate response and increased efficiency in the muscle in over 90% of the cases. And when combined with specific movements, such as lunges or squats with the application of electrodes in working muscles during those exercises, there was improved MPL/MTL in every case.

B. Electrical Stimulation: Components, Electronics, Techniques, and Parameters

Example 2

In FIG. 9, electrodes 907, 908, 909, 910, and 911 comprise a network of electrodes that are carefully placed on various parts of the muscles. By sending the multiple electrical currents of sound waves wherein the pulse of the second wave syncs with the nerve's action potential, a varying level of intensity are felt by the patient. The patient can provide feedback to the technician verbally as to which feels stronger (much like optometrist asks which lens allows a patient receiving corrective lenses to see letters more clearly). The patient can also provide feedback in relative portions saying in a scale of 1 to 10 how much pain is felt. Ideally, box 903 will measure the relative discomfort felt at each location on the array of electrodes and store/process that information to aid in finding the areas of muscle inefficiency. Using conventional recording systems, such as a microprocessor, memory, a motherboard, RAM, basic firmware, such parameters of pain or discomfort thresholds can be measured and recorded. In objective parameters, discomfort is associated with increase in heart rate, or decrease in heart rate variability, or increase in perspiration (or breathing rate, or blood pressure, or a decrease in oxygen saturation rate, or galvanic skin responses which increases surface electrical conductivity as perspiration increases) during higher levels of discomfort. In other words, if the muscles are inefficient, the body will respond with "protective mechanisms" that include perceptions of discomfort, which will increase the heart rate, blood pressure, breathing rate, and increase the level of perspiration. If this is measured using a computer processor over a long period of time, e.g., 5 minutes, or 10 minutes, or 20 minutes, or 1 hour, or 4 hours, or 24 hours, or longer, there can be a consistent mapping of the heart rate associated with the muscle inefficiency. In other words, let's say that electrode 907 is turned on and the recipient experiences a subjective 5 out of 10 discomfort. If stimulation through that electrode 907 is continued, there will be an increase in heart rate associated with the inefficiency of that muscle. The more inefficient the muscle, the higher the heart rate. The higher the power, the higher the heart rate. So, if we maintain the same power and current and provide the pulsed second frequency, there will be an increase in the heart rate over time, such as 30 seconds, or 2 minutes, or 5 minutes. If electrode 907 is then turned off and electrode 908 is turned on at a different area of the muscle, and if the patient then experiences discomfort on a subjective level that is 7 out of 10, then the technician can isolate the location of the muscle inefficiency. In addition, because of the higher level of subjective discomfort, there is likely to be a natural higher level of heart rate and higher level of perspiration. If the level of perspiration can be measured using a simple circuit and if a standard heart rate monitor is used in conjunction with the different electrodes being turned on and off, there can be a precise mapping of the muscle areas that experience higher levels of inefficiency, and a way to objectively quantify information that would otherwise be very subjective and difficult to track.

Box 903 will also have conventional means to measure heart rate, heart rate variability, blood pressure, blood oxygen saturation level, skin conductivity, and/or breathing rate. For purposes of identifying "matches" these levels can be measured manually. "Matches" means the ability for the pulse frequency to match natural action potential frequency. The depolarization of a neuron caused by the stimulus above the threshold voltage results in a complete action potential (i.e., it is all-or-nothing). If the stimulus strength is increased, the size of the action potential does not get larger. The size (i.e., amplitude) of the action potential of a given animal is generally the same and independent of the size of the stimulus, but small variations exist between different animals. The nervous system creates stronger muscle responses by increasing the frequency of the action potentials. Thus, the stronger the stimulus, the higher the frequency at which action potentials are generated. Therefore, the frequency of action potentials is directly related to the intensity of the stimulus. However, as described in prior art references like U.S. Pat. Nos. 5,107,835 and 5,109,848, which was published in 1992 or U.S. Patent Application No. 20130060304, there has never been any attempt to match the changing frequency during the application of the direct currents. It is shown that increasing and varying the frequency (in a diagnostic process) can suddenly find the optimal frequency at which the body recognizes as "normal." In other words, during the exercise of a certain muscle movement, the frequency of the muscle will increase relative to the needed exertion of the muscle. The current invention challenges traditional notions of "cellular disruption" and tries to find the "sweet spot" of frequency that best matches the actual frequency the body would produce if the muscle were behaving efficiently.

All the examples used in the disclosure use the multiple frequencied machines, but there are more than one way to put together a machine that can produce one set of electrical currents (direct current) at a sound frequency level of 20 hz to 20,000 hz and then another pulsed set a different rate, the difference in the level should be equal to or higher than the action potential reaches of range. For example, in a neuron of a human, −70 millivolts (mV) is the peak and the threshold potential is around −55 mV. The membrane potential abruptly shoots upward, often reaching as high as +100 mV. So, the range is around 170 millivolts. The frequencies for both the resonating and the pulse must accommodate for the range in voltage patterns.

Figure 6:
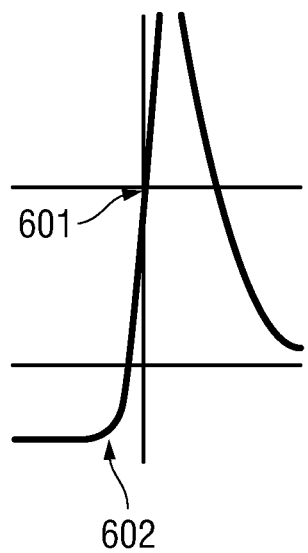
FIG. 6 shows an illustration of a peak following the downward slope in the prior art system disclosed in the 1992 system.
Figure 7:
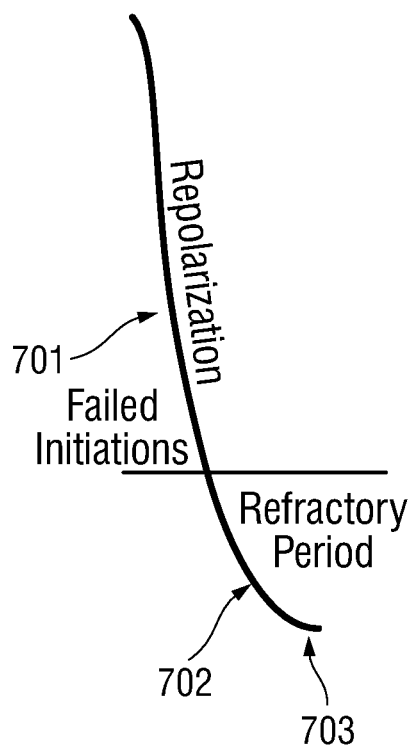
FIG. 7 shown the downward slope of a natural action potential shown a sharp decline in the exponential decay.
Figure 8:
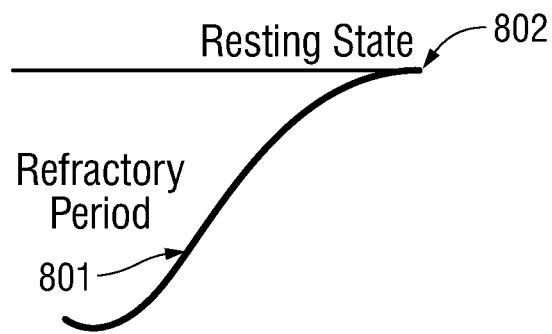
FIG. 8 shows another embodiment of a natural action potential shown an S pattern wherein a distinguishing element in a natural action potential is the resting period and the ability to efficiently generate a quick signal of varying degrees using the resting period as a baseline.

In U.S. Patent Application 20130060304 titled "Method and Apparatus for Generating Electrotherapeutic or Electrodiagnostic Waveforms" there are clear methods of providing multiple frequencies and ones within the range of sound frequencies. This application has a FIG. 6 within its disclosure that teaches the disclosure of patterns that even resemble refractory sections, but there is no disclosure that the motives are to mimic the action potentials, and the current invention also discloses the ability to separate the two sets of frequencies so that one syncs with the body and the other syncs with the nerves in a manner that pulses signals are identified by patients as nerve action potential signals. Doing so has resulted in immediate accelerations of healing and gains in performance. In 100 patients studied, 99 feel immediate improvement in muscle activation, manifesting as force being absorbed back on the muscles that were inefficient beforehand and a sense of greater ease or less pressure in the relevant joints. In training, the results show over 65% improvement when compared to conventional weight lifting or nautilus-style gym equipment training. In therapy, the reactivation of muscles to take on their force absorption role allows them to naturally protect an injured area while it heals, resulting in over 60% faster healing times.

In animals, the location of injuries has been identified by use of electrode placements and mapping of heart rate increases in over six different muscle groups. In each of these cases, there were increased mobility in the injured areas at an improvement of over 50% compared to conventional means of casting and other forms of immobilization of the joints and muscles. There are direct evidence supporting concepts that the action potential and ability of the brain to sync with the action potential of the muscle is required for the body to properly heal or make the muscles more efficient. Once the muscles are more efficient, the body naturally addresses any injured joints and ligaments, whereas in immobilization or casting techniques the healing process is prolonged and cannot complete until much later when the body is able to re-engage the muscles. Theoretically, even in the case of a broken bone, if the muscles around the broken bone are fully engaged, it can absorb a large fraction of the forces that bone supports, and doing so may in some cases actually allow the bone to heal faster than traditional methods involving casting.

In FIG. 9, the box 903 shows a device which may comprise a medical or therapeutic device, according to an invention that identifies inefficiency in muscles and that heals inefficiency in muscles. Box 903 provides a waveform to a patient according to any of the embodiments in the current invention. The waveform may be generated based, at least in part, on a digital signal downloaded from the Internet via Internet connection or downloaded from another source via USB port. Such a digital signal may comprise an electronic file that includes computer-readable code representative of one or more waveforms.

A waveform may attain any of a number of shapes. For example, a waveform may comprise a sinusoid, a square wave, a sawtooth wave, a low-duty-cycle pulse, microcurrent wave, or an arbitrarily-shaped wave. A waveform may comprise one wave shape (or other parameters) for one time span, another waveshape (or other parameters) for a subsequent time span, and so on. Variables of waveforms may include time between pulses, pulse duration, duty cycle, shape of pulses, frequency modulations, amplitude modulations, pulse width modulations, ramping, peak on-times, surging, decay rates, and so on. In the example shown, waveform may comprise a pulse including two peaks. Such waveforms are merely examples, and claimed subject matter is not limited to any particularly-shaped wave or signal.

Box 903 may include a screen, which may comprise a touchscreen, for example. Box 903 may include a number of switches, knobs, or keyboard to allow a user to manipulate the device, input patient information, adjust parameters of a waveform, and so on, for example. A waveform file executable by device may include instructions regarding sensitivity or functionality of any of switches, knobs, or keyboard, for example. Such instructions may also be executable by device to operate the screen with particular features or have particular functionalities.

A waveform may be described by any of a number of techniques. For example, one or more mathematical equations may describe, at least in part, a waveform (e.g., amplitude multiplied by a cosine function having a particular frequency, or a series of sinusoidal functions respectively having varying frequencies or amplitudes). In another example, a table of values may describe a waveform. Such a table may include wave amplitude as a function of elapsed time of a cycle of the waveform In U.S. Patent App. No. 20130060304, there is a disclosed a "waveform code" comprising an exponentially-rising/decaying pulse having a frequency of 500 hertz (Hz) for 2.0 seconds, the exponentially-rising/decaying pulse having a frequency of 800 hertz (Hz) for 10.0 seconds, the exponentially-rising/decaying pulse returning to a frequency of 500 hertz (Hz) for 2.0 seconds, which repeats. Conventional pieces of electronic components can be added to make both frequencies. First, there has to be a direct current converter and a splitter or an ability to have two sources of direct current.

Figure 11:
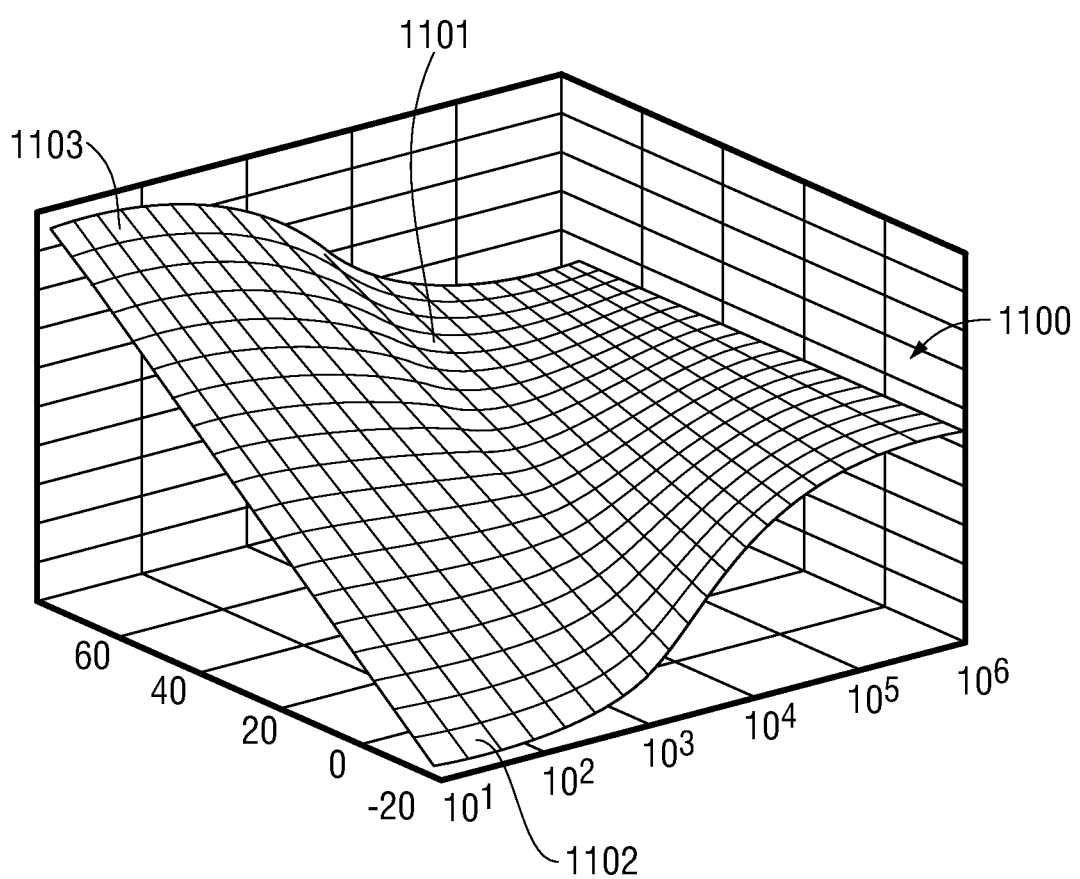
FIG. 11 shows a 3D map of areas where intensity or heart rate increase is associated with either different electrode locations or different power/wavelength forms provided to a patient that isolates and locates the particular area of inefficiency.

With the ability for the device to generate different waveforms having different shapes, magnitudes, and frequencies (for purposes of describing a machine that can alter the waveform patterns, U.S. Patent Application No. 20130060304 is hereby included within this disclosure).

Where U.S. Patent Application No. 20130060304 falls short is the following:

Harmonizing the first set and second set of frequencies such that the first set syncs with the body (outer epidermis, bones, fat) and a second pulsed set that resonates with the nerve and has the ability to mimic the action potential. U.S. Patent Application No. 20130060304 does not try to achieve the mimic of the action potential. Because there exists the ability to quantify muscle inefficiency using the techniques of this invention, there is the ability to alter the pulse delays or patterns or heights so that the increase in heart rate or increase in subjective discomfort levels can be associated with better resonating matches of the action potential. The level of achieving the harmony with the natural action potential from U.S. Patent Application No. 20130060304 is not achieved or may be intermittently coincidental, but the current invention enables an isolation of the muscles that are inefficient and it also enables a standardization of muscle inefficiency so that the second frequency can better mimic the natural action potential of the selected nerve that is attached to the selected muscle. Even over U.S. Patent Application No. 20130060304, improvements in matching the action potential signal has resulted in surprisingly over 23% better efficiencies in over 60 patients studied when compared to control patients. This is due to scientific understanding that when the frequencies actually match patterns of action potentials that are generated naturally during specific body movements, the brain is "rebridging" the connection between the brain and the muscle, which normally exist in more efficient muscles;

U.S. Patent Application No. 20130060304 does not disclose the isolation of muscles using subjective input or objective input (e.g., heart rate average increase over 2 minute intervals) by using different electrodes or different electrode locations and then determining the intensity and then creating an array map. For example, in FIG. 16, the array of a mapped out area is shown that covers the quad area of the leg. Bendable areas 1603 and 1606 allow the leg wrap to bend and knee hole 1607 allow the leg to move and breathe. The electrodes in 1601, 1602, 1604, 1605, and 1608 can be calibrated with a technician or a computer to take in the levels of intensity that can be measured by subjective or objective standards described in Table 2 above. In the case of subjective input, the level of intensity can be measured by grip pressure or verbal expression on a scale of 1 to 10. In the case of objective input, a longer area can be spanned using multiple electrodes or careful location selection of the electrode and placement on a muscle so that an increase in heart rate or change in other physiological parameter can be associated with a more injured muscle or a more inefficient muscle. Because there is a basis to standardize the muscle inefficiency based on this disclosure, there is a manner to create a map showing precisely what part of the muscle needs work. Because of the precision of this method, in over 500 patients studied, the improvements in isolating and addressing muscle inefficiency is enhanced by over 40% compared to the traditional methods, such as used in disclosed in U.S. Pat. Nos. 5,107,835 and 5,109,848, which was published in 1992 or U.S. Patent Application No. 20130060304. The references of U.S. Pat. Nos. 5,107,835 and 5,109,848 show ways that multiple frequencies can be added in a direct current having pulsed patterns in the second frequency, and because these references also disclose traditional methods of creating these direct current frequencies, these references that are now in the public domain are included herein for their reference and disclosure of these frequencies. In FIG. 11, high level 1103 is associated either with subjective input from patients showing high level of intensity or discomfort or in the objective input from higher heart rate averages over a longer period of testing time.

U.S. Patent Application No. 20130060304 does not actually mimic the action potential, but the current invention uses the same range coverage of nearly 150 mV that an actual potential range covers. These references are all about trying to trigger the action potential. If the machine triggers the action potential with a pulse, then the application in U.S. Patent Application No. 20130060304 has done its job. Unlike these prior art references, the current invention mimics the action potential so that the brain recognizes the pattern. It does not need to actually trigger an action potential, as the appropriate biological adaptations will occur as long as an action potential signal is received by the brain. When combined with exercises or movements that normally do trigger these action potentials, then the ability exists to rebridge the brain's connection to the under active muscles. The current invention mimics the actual number of mV by reversing the wave form of direct current such that it produces the negative 90 mV necessary to mimic the refractory period of a real action potential. No other disclosure does this, and by comparison, the mimicking of an actual action potential has resulted in even faster rates of recovery with up to 80% improvement over these prior art techniques.

Figure 12:
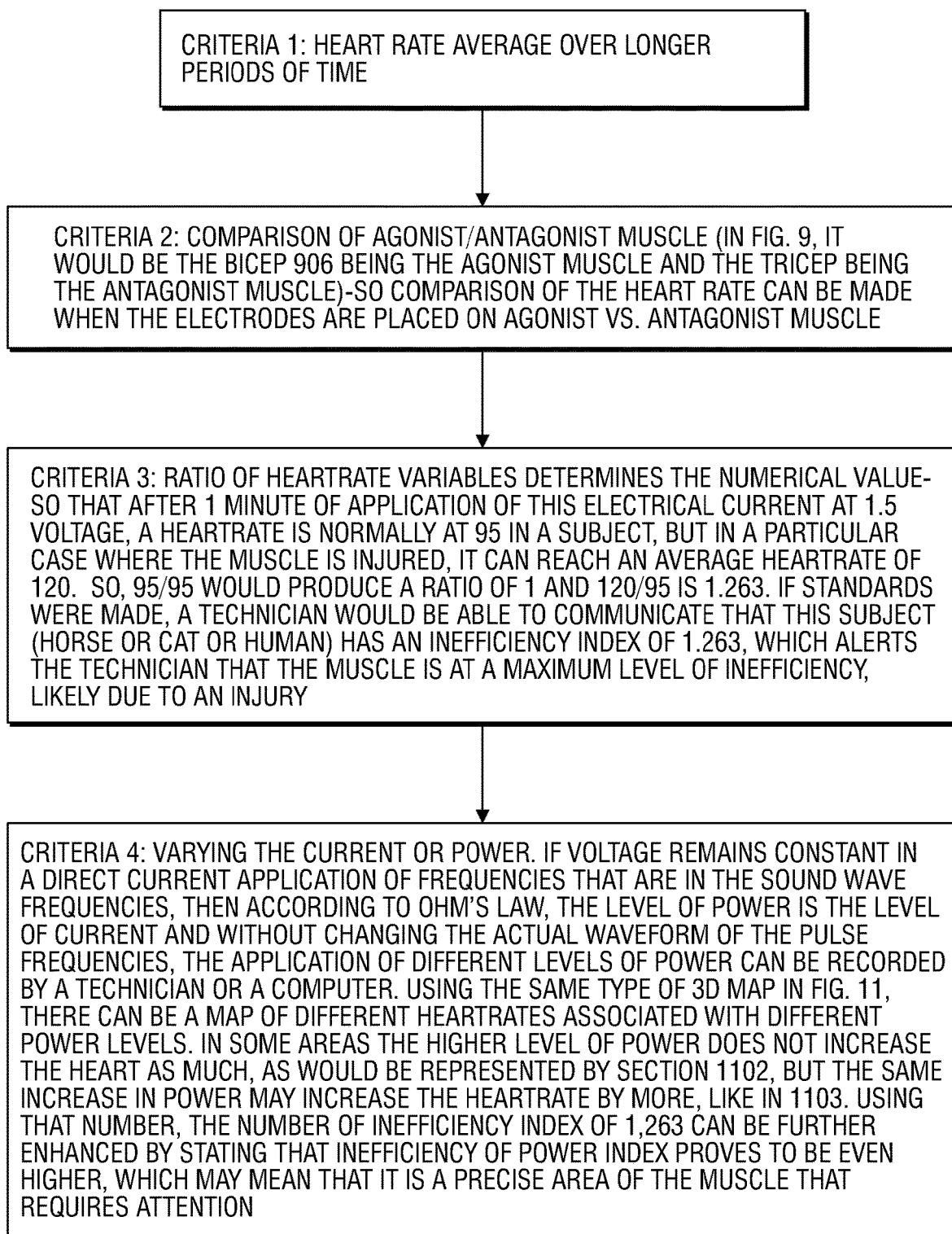
FIG. 12 shows a basic representation of how a factor from each criteria in Table 2 can be created for consideration in developing a standardized form for measuring, tracking, determining, and improving muscle efficiency.

Up to now, there has not been a standardized method to determine muscle efficiency. Although almost any person can subjectively determine when a muscle feels weak or when a muscle is not working right, doctors or technicians currently have no parameters to objectively determine muscle efficiency. In other words, doctors cannot communicate with each other the level of disconnection between the brain and the muscles, which in many cases is the reason why a subject feels pain (especially when force that should be absorbed in muscles is transferred to joints and ligaments). By using objective measures, such as heart rate average, or subjective measures, a system of comparing that threshold number with either its antagonist muscle, or opposite body muscle, or previous sessions, or values of other users in a database, can determine the health of that muscle. For example, in a thoroughbred horse that has had a full diagnostic, baseline reading with average heart rate measures at a certain power of the box 903 and application of the action potential mimicking frequency, if the thoroughbred horse has an injury such that running another diagnostic increases the heart rate at certain electrode locations, a technician may be able to isolate the actual injury without having to "read" the horse or take any x-rays or MRI images of the horse. Further stimulation of those muscles found to be affected will mimic the actual action potential and re-engage those recently disengaged muscles. This stimulation will repair the bridge between the brain and those muscles, and, surprisingly, this approach leads to increases muscle efficiency that are over 35% greater in human and animal subjects than can be achieved with conventional stimulation devices, including devices disclosed in U.S. Pat. Nos. 5,107,835 and 5,109,848, which was published in 1992 or U.S. Patent Application No. 20130060304. Table 2 of the current invention shows different permutation capabilities for determining a numerical value. One can use one or more items from each Criteria to derive a standardized formula for muscle efficiency. Because there has been no effort made in this field, the current invention leaves open the possibilities of using these or other derivative methods to come up with a standardized methods of muscle efficiency. As an example, in FIG. 12 takes into consideration "Objective: heart rate increase over period of time and address the increase in heart rate over different areas of application" of Criteria 1 in Table 2. It then takes "Measured agonist/antagonist muscle" element of Criteria 2 in Table 2. It then takes "Ratio of Heart Rate variables" of Criteria 3 in Table 2. It then finally takes into consideration "Vary Current (or power)" of Criteria 4 in Table 2. Using these criteria, FIG. 12 shows how a standardized form of muscle inefficiency can be determined. In combining these, a new index can be formed that takes into consideration each of these four criteria. What is important is that there is a means by which a standardized form of measuring muscle inefficiency can be achieved—objective input and subjective input considerations are taken into consideration.

A further distinction is the useful manner in which a sync with an action potential can provide unique training and healing methods that, when applied to certain movements or exercises, creates a further enhancement of the brain's ability to re-bridge its connection to these muscles. Thus, the application of these specific frequencies when combined with unique techniques can provide drastic improvements in muscle efficiency. In over 500 patients studied, mobility increased 95% faster using these techniques than with traditional physical therapy. In these same patients, over 15 surgeries were avoided based on the ability of the brain to re-engage with these muscles. Methods are described below.

It is well known in the industry to take into consideration patient information such as body weight, age, sex, heart condition, injury status, injury/health history, and history of treatment using box 903. But considering the 3D capabilities of being able to precisely isolate muscles and because there now exists a way to track progress in muscle efficiency based on Table 2 considerations, patient information takes on new meaning. Patient information can be used as the baseline information to form an efficiency measure. For example, based on Table 2 criteria, a patient may have an inefficiency index in the biceps of 1.1 one week and 1.05 the next week, which for purposes of this example means that there is an increase in efficiency (less heart rate for the same application of power for the same muscles). Such considerations are especially helpful in the context of animals or patients that are unable to communicate or locate the pain, and can also be helpful to measure subtle changes that indicate improvement in function but may not yet be able to be perceived by the patient. In over 15% of the cases of 500 patients studied, techniques used in standardized methods of Table 2 actually resulted in location of the weakened or inefficient muscle when other physicians were not able to locate it.

A processor can manipulate the waveform, but the array creation of different power levels or considerations of this application are novel. Because of the ability to create a 3D map and the ability to standardize muscle efficiencies, there is potential in individualizing care with algorithms. After the isolation of the muscle inefficiency in patients, a technician will then have an understanding of where to treat the muscles (precisely) and what parameters to use (e.g., power and isolation of mimicked action potential).

Figure 1:
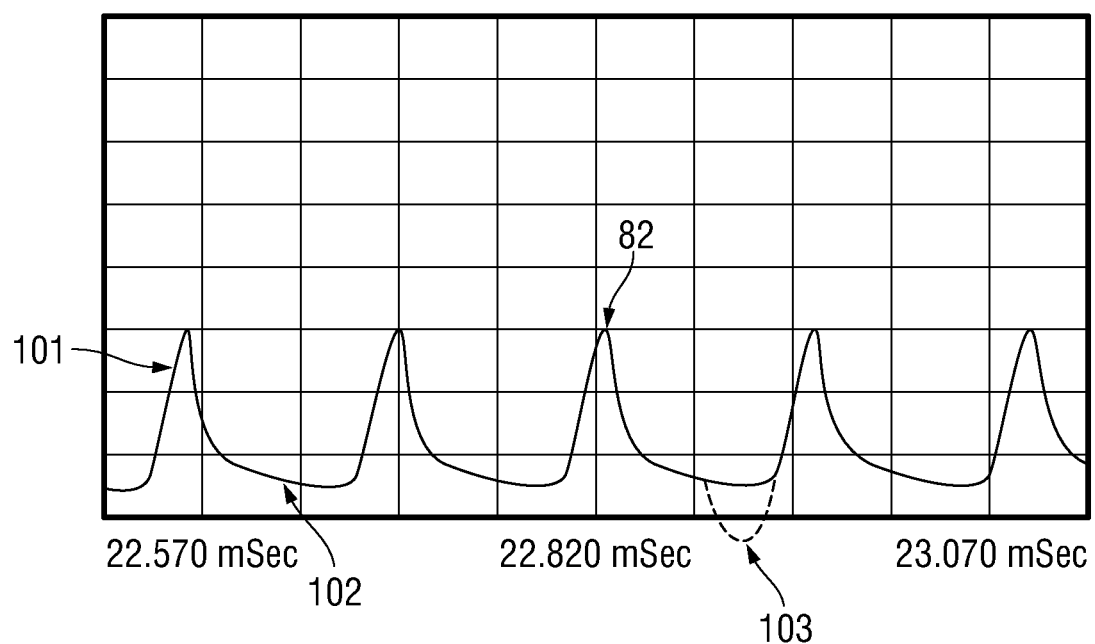
FIG. 1 shows a prior art voltage reading of a direct current electrical current used to stimulate the body that was well known by 1992.
Figure 2:
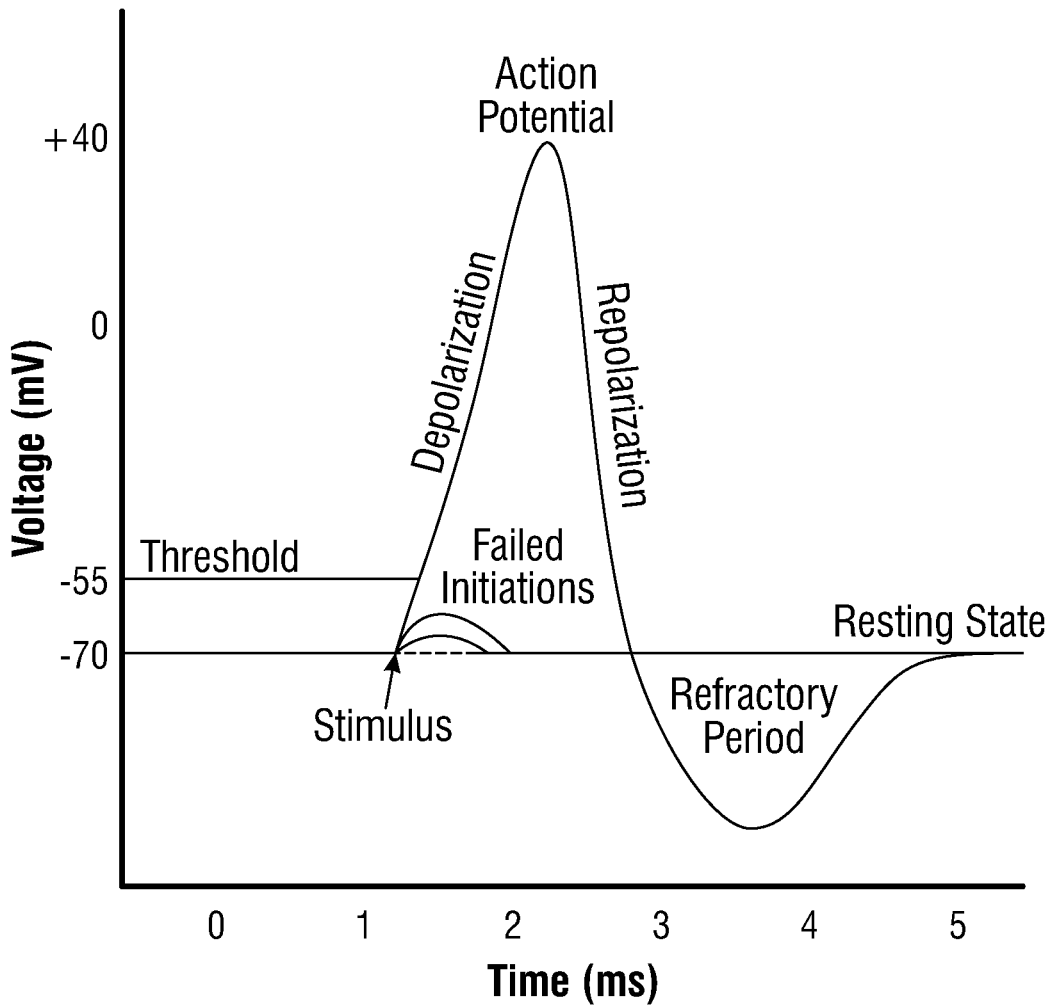
FIG. 2 shows a classic form of action potential of a sodium ion channel nerve response showing the voltage with the action potential and refractory period.
Figure 3A:
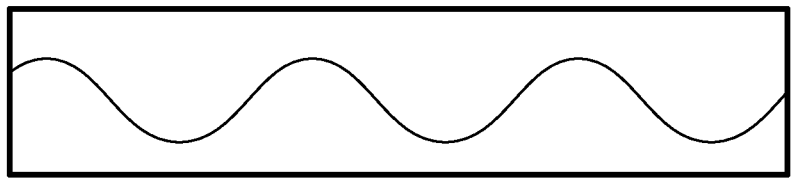
FIGS. 3A to 3F show six different shapes of waveforms wherein 3E represents a rising exponential waveform and 3F shows an exponential decaying waveform.
Figure 3B:
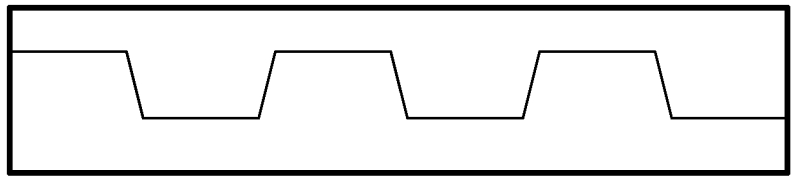
Figure 3C:
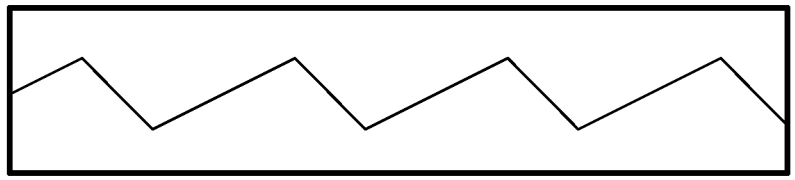
Figure 3D:
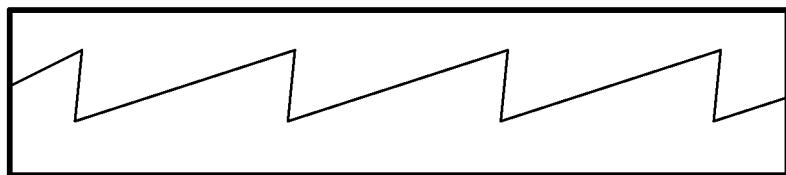
Figure 3E:
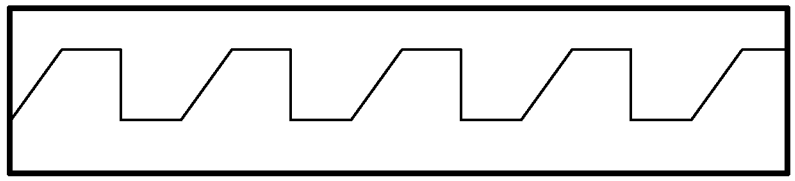
Figure 3F:
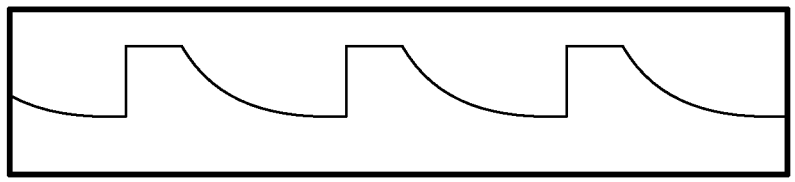
Figure 4A:
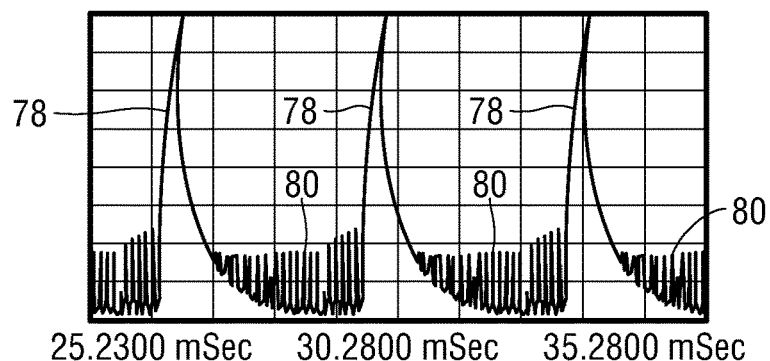
FIGS. 4A-4C shown prior art attempts of creating a pulse with a direct current showing peaks wherein none show any of the classic waveform as in the action potential, refractory period, and resting period to show the response as shown in FIG. 2.
Figure 4B:
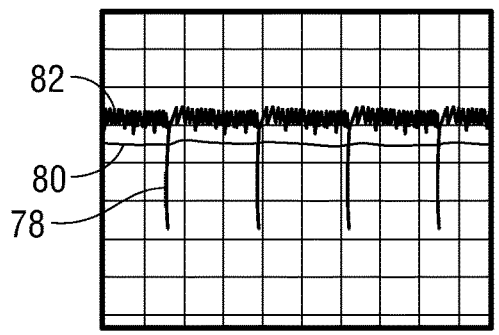
Figure 4C:
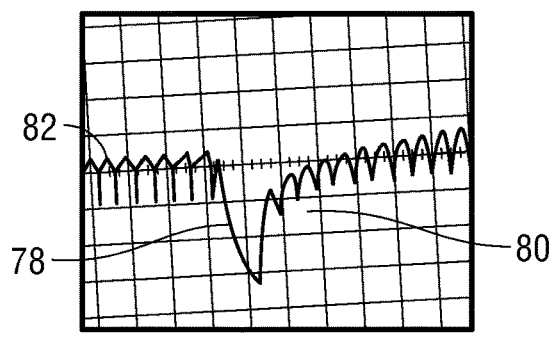
Figure 5:
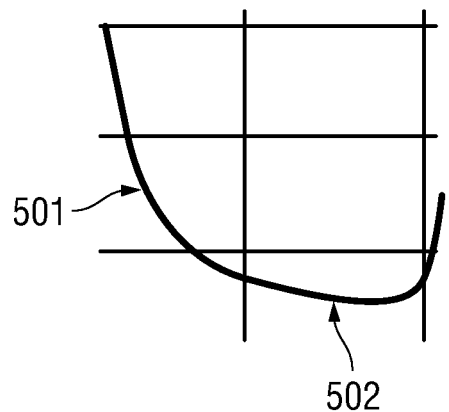
FIG. 5 shows a downward slope of a pulse used by direct current shown an exponential decaying waveform in a prior art system disclosed in 1992.
Figure 10:
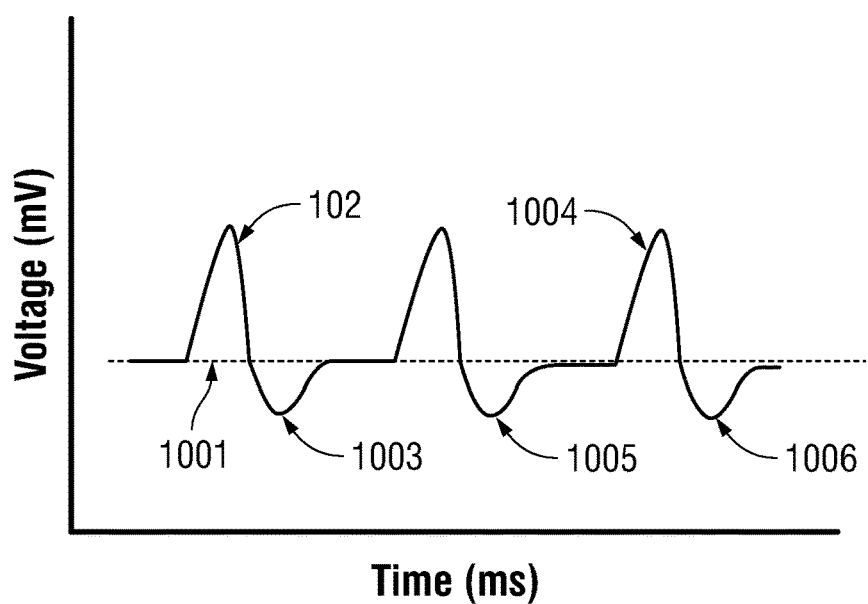
FIG. 10 shows the pulsed second wavelength waveform according to one embodiment of the current invention.

FIG. 10 shows the second wavelength waveform according to one embodiment of the current invention. The pulses resemble action potential shown in FIG. 2, which shows the polarization rise 1004 of the action potential shape and the depolarization downward shape 1002, and it has a refractory section 1003 and notice that these pulses are sent in order so that refractory section 1005 is the same. The refractory section 1006 has a slight downward path as in the real action potential. In other conventional systems that use pulses of direct current, none have shown to mimic the action potential. The repeated pulses produce a baseline at 1001, which means that to the body, the brain receives continued pulses of forced action potentials. If the muscle is healthy, the action potentials only reproduce the natural pattern of activation of these action potentials, and no rise in heart rate is felt when the level of stimulation matches that of normal activity. If the muscle is not healthy, or inefficient, the brain has an inability to properly process these action potentials themselves, which means that the brain resists these patterns of action potentials, and creates discomfort or a rise in heart rate or other neurological response, all in its attempt to limit or reduce the activity of the inefficient muscle.

If there is injury or some form of damage in this area, the body then naturally address these concerns because this signal applied during treatment of the effected areas causes the brain to become more aware of that area of the body and any repair work that needs to be done there. As a result, in areas that are recently injured, the body will be stimulated to activate the biological processes and send the resources necessary to heal these damaged areas much faster. Even in injuries that are many years old and have not fully healed, the stagnant healing process can be re-engaged and stimulated to move towards completion.

The improvements in muscle efficiency described above provide a foundation for an efficient healing process. As these muscles work properly, they can form a natural brace or shield around an injured area to protect it against further damage while it is healing. Combining that foundation with the acceleration of biological healing processes, the body has been proven to heal from a wide variety of ailments 30 to 70% faster than with traditional methods.

When training for athletic performance, stimulating diverse areas of the body with the multiple electrical waves of sound wave frequency evokes the same natural reaction of the body to make these muscles more efficient. This effect has been proven to heighten the performance of these muscles to enhance overall athletic performance. For example, an athlete performing bench presses or squat jumps can activate the necessary muscles, at the appropriate time and in the appropriate way, to achieve immediate improvements in muscle output that lay the foundation for more efficient gains of muscle tone, mass building, flexibility, strength, speed, and power. Often, this is accomplished by an actual enhancement of the nervous system. This type of stimulation can trigger restructuring of neurological synapses and the preferential deposition of myelin to improve the performance of the specific pathways that are stimulated.

C. Quantitative Measurement of Efficiency

By mimicking the action potential, the next stage is actually to perform various movements that coordinates the general firing of the action potentials in a more efficient muscle. In other words, if the muscle was efficient, the action potential would generally be moving down the nerves, but because of some form of injury of inactivity or misuse, there arises the occasion where the brain does not fire the action potentials to these muscles in a normal, general pattern. In these case, the use of a mimic potential can provide the ability to accelerate the brain's ability to re-engage and bridge the brain's communication to the inefficient muscles. When these inefficient muscles are stimulated with a direct current waveform in the shape of an action potential, the results show an improvement in over 80% of its patients. And in 100% of the patients, there has been a 75% measurement of healing to full efficiency from other controls.

As shown in Table 1 (Muscle Efficiency Measurements using the action potential mimicked patterns):

| Patients | % Improvement in Initial Treatment | % Maintained Improvement in Second Treatment | % Maintained Improvement in Third Treatment | % Maintained Improvement in Fourth Treatment | % Maintained Improvement in Fifth Treatment |
|---|---|---|---|---|---|
| 100 Female | 90 | 80 | 50 | 70 | 80 |
| 100 Male | 90 | 75 | 54 | 77 | 88 |
| 100 Female (Objective) | 90 | 75 | 60 | 80 | 90 |
| 100 Male (Objective) | 90 | 80 | 60 | 85 | 92 |

Table 1 is a measurement of muscle efficiency improvement by methods used in this disclosure. The treatment of these patients were a combination of the matching of the action potential of the electrical direct currents in combination with various exercises that would naturally change the frequency of the muscles during the exercise. Muscle efficiency is a term of lexicon used in this application to mean the ability of the brain to communicate with the muscle in a normal fashion wherein a normal communication between the brain and the muscle allows for the transmission of signals that permit the muscle to extend and contract quickly. The determination of these characteristics in the natural setting is the ability to send the waveform of the action potential in various frequencies to the patients. These measurements were made using subjective tests and objective tests. The methods used in combination with the particular individualized delivery of a waveform in the shape of an action potential demonstrate increases in muscle efficiency for both the subjective tests and the objective tests. In many ways, the subjective tests can described as so: stimulate the patient's body with a direct current according to the embodiments of the current invention. Because of the multiple electrical currents at sound frequency pulses mimic the natural action potential, areas of muscles wherein there is inefficiency (or areas to which the brain has a less than normal ability to send proper action potentials) provide discomfort because these action potentials are behaving as if the muscles were fully efficient and engaged. By changing the frequency of the electrical current pulses, there is associated match when the discomfort or the objective tests show the highest results. In other words, with the proper frequencies sent during proper movement of the muscles, there will be pain or discomfort in proportional measures according to how under active or inefficient the muscle is. The more inefficient the muscle, the more discomfort from the frequencies of these waves. But up until this invention, there had not been any scientific or statistical ways to use this information. And up until this invention, there had not been ways to better mimic the action potential such that the feedback can provide faster rates of muscle recovery.

Based on the body's reaction to the application of the reproduced action potentials at direct currents and the mimicking of the action potentials using precise locations and precise movements, a standard can be derived that determines muscle efficiency or muscle inefficiency. Because of the variations that exist between individuals and in muscles, there are variations on certain criteria that can combined to derive at a standard. Table 2 shows four of those criteria, and according to embodiments of the current invention, anyone element in each criteria can be used to derive a standard for muscle efficiency/inefficiency. According to embodiments of the current invention, one or more criteria can be used and as many as four or combinations of more than one criteria to derive a baseline of muscle efficiency such that future determination can be calculated.

TABLE 2

CRITERIA 1
STANDARD (TYPE OF INPUT FOR
DETERMINING MUSCLE INEFFICIENCY)

Subjective: measurement of discomfort or pain from a scale (like 1 to 10) by different areas and then mapping out the degree of pain from each area
Subjective: asking patient to grip harder or bite harder and record the strength of pressure vs. different areas of application
Subjective: User push button asking client first feeling of pain and moment of intolerable pain, push button may also be a kill switch
Objective: heart rate increase over period of time and address the increase in heart rate over different areas of application
Objective: heart rate average over longer periods of time while current is applied to different areas creating a map of discomfort
Objective: use of forced contractions and feedback from contractions (do we need to add breathing rate, perspiration, blood pressure, etc. here to cover our bases for other potential criteria for measurement??)
CRITERIA 2
BASELINE CONSIDERATIONS FOR MUSCLE INEFFICIENCY Measured agonist/antagonist muscle comparison
Muscles can be compared from left side and right side

TABLE 2-continued

Muscles can be compared from previous uses and statistical
models showing history
Muscles can be compared using database
Muscles can be measured immediately every X seconds and resets

CRITERIA 3
MEASURING FACTORS/DATA

Heart Rate Max, Ratio of Heart rate variables
Ratio of Max Discomfort Level to Lowest Level of Paint
Comparison to Database of Standards
Constant Measurements X seconds heart rate
Heart Rate Variability

CRITERIA 4
HOW TO INDIVIDUALIZE THE
REPRODUCED ACTION POTENTIAL TO MIMIC

Use Action Potential Shape and get feedback
Use same voltage and frequency range as real
Action Potential and get feedback
Vary the frequency during stationary positions for various
periods of time (1 second to 5 hours)
Vary Current (or power)
Vary the frequency during exercises wherein the
variance of the frequency match an exponentially
rising curve as the real action potential during the
contraction of the muscle during the movement Table 2 shows permutations on how to calculate inefficiency in a muscle; by doing so, other methods of muscle inefficiency diagnostic testing is derived, and such can be used to calculate other useful data for purposes of treating muscle inefficiency. The following are mere exemplary and can be derived from the above information.

The match is determined by subjective or objective results of varying the frequency slightly in a 150 mV range and changing the on/off of the powerful in a pattern that provides electrical current in periodic forms. This does two things: first, by varying the frequency, every time the frequency matches with the body's actual frequency used in the exercise, there is exertion. This is shown in Table 3 below:

| Difference in Frequencies used in Second Pulsed Frequency | Heartrate Variability (per minute) | Breathing Rates (times per second) | Blood Pressure (standard) | Perspiration Rate (based on galvanic test) | Oxygen Saturation Rate (% Increase) | Subjective Grip Pressure (% grip of pressure of full pressure grip) |
|---|---|---|---|---|---|---|
| −50 mV | 90 | 23 | 140/70 | 10% | 0% | 15% |
| −25 mV | 90 | 24 | 140/70 | 10% | 0% | 25% |
| 0 | 105 | 35 | 160/90 | 15% | 10% | 85% |
| 25 mV | 105 | 35 | 165/96 | 15% | 15% | 95% |
| 50 mV | 95 | 27 | 140/75 | 11% | 7% | 40% |
| 75 mV | 95 | 25 | 140/75 | 11% | 5% | 30% |

Using the objective measure to determine muscle inefficiency has many benefits. First, because it is using an objective test, the level of muscle inefficiency can be measured objectively over a given period of time without any verbal or subjective input from the patient. If the patient is unable to speak (autistic, infant, or animal), the rise in heart rate associated with the different patterns of electrode stimulation provides objective measures on exactly the location of muscle inefficiency. This muscle inefficiency is not the normal contraction of muscles that are provided by conventional medical electrode devices using alternating current. Instead, these muscle inefficiency stimulations mimic the action potential, causing the brain and nervous system to believe that muscle is actually moving, and responding to either permit that movement or attempt to "protect" against it. If you provide this application to thoroughbred race horses or dogs or cats or any veterinarian clinic, the use of a machine that can map out the different heart rates using direct current without the contraction of muscles can slowly but very accurately provide a computer or a technician a map of muscle inefficiency. Combine that with a numerical standard by which a muscle inefficiency can be determined, there is now a new method of determining whether an animal or patient is hurt without any communication. A patient that is in a coma or an elderly patient that is unable to communicate can attach the electrodes and by slowing changing the different levels of electrode stimulation in electrodes 907, 908, 909, 910, and 911, a technician can now accurately determine the level of muscle inefficiency. Because injuries cause muscle inefficiency, in short, using the standards and techniques in this disclosure, there is now an objective, diagnostic tool that can measure an injury of animal or patient even without any input for the patient or animal.

Example 3

By tracking improvement in muscle, the determination of muscle level efficiency and level of healing can be empirically determined (empirical in the sense that results are objective and can be proven scientifically). Because there is a unique application of multiple electrical currents that mimic the action potential in this current invention, these are not the same as alternating current electrodes that contract muscles, and which are available in many hospitals or medical facilities. The application of these frequencies do at least two things differently: one set of frequencies at a sound wave harmonizes or resonates with the body, which is comparable to a sound wave that can trigger a resonator. While this one set of frequencies do this, another pulse set mimics the action potential and sends signals from the associated muscle. If the muscle is healthy, the sending of another action potential does not provide any discomfort at all to the patient. If the muscle is not healthy and brain is not efficiently engaged with it, than sending an action potential down the line creates a "protect" response and a brain signal which short circuits the connection and provides a sense of exertion on the muscles (which sometimes is, although not necessarily must be a contraction). Doing this causes the heart rate to go up when the muscle is inefficient, just as it would in response to any physiological stressor. And the inefficiency again can be measured by comparisons to other databases of normal levels or prior uses that determine a baseline of normal or comparisons of other sets of agonist/antagonist muscles, or comparisons to the same muscles on the opposite side of the body, or baseline comparisons from previous test sessions. What is important is that by using these multiple set of frequencies, a technician can now derive a standard by which muscle efficiency can not only be determined, but also translated easily.

D. Quantitative Results and Data Supporting Invention and Associated Research Physiologically, action potential frequencies of up to 200-300 per second (Hz) are routinely observed. Higher frequencies are also observed, but the maximum frequency is ultimately limited by the absolute refractory period. Because the absolute refractory period is ~1 ms, there is a limit to the highest frequency at which neurons can respond to strong stimuli. That is to say that the absolute refractory period limits the maximum number of action potentials generated per unit time by the axon. As described previously, the strength of the stimulus must be very high in order to ensure that the duration of the action potential is as short as the duration of the absolute refractory period. A stronger than normal stimulus is required to overcome the relative refractory period.

Because the absolute refractory period can last between 1-2 ms, the maximum frequency response is 500-1000 s-1 (Hz). According to results of Table 3 and other clinical data, the level of matching the actual action potential frequency with the activity so that the activity would normally produce that frequency produces the highest rate neuronal feedback response. As shown in Table 3, there is noticeable difference in each of the tests (breathing rate, blood pressure, heartrate, perspiration, and the subjective tests) when the frequency of the second pulse is varied at 5 minute intervals at slight variations of the frequency. At 0 and 25 mV, there is noticeable spike in the match. This match is the recognition of the body that the frequency is normally at that frequency.

During movement, this frequency will change depending on the level of muscle needed for the movement. However, there has not been any current studies showing the matching of the frequencies with the action frequency change of the movements. The current invention shows that by varying the frequency, there is a noticeable matching that tells the technician at which the maximum level of recognition of action potential by the brain is recognized. And to increase the current, or power, at that isolated frequency would coordinate with the brain to re-engage these muscle. When the movements or exercises are timed so that the contraction of the muscles are timed in intensity with the level of power at matching frequencies, then clinical evidence shows significant increases in over 60% improvement of muscle efficiency.

The second pulse frequency can also be switched on/off in a repeatable pattern (high speed). Although it may not match the same frequency, the level of turning on/off allows the body to pass through the natural frequency more often considering it passes through the frequency during each initiation of the on button.

The reproduction of the action potentials and the reproduction of the varied frequencies to natural action potentials are considered "matching" for purposes of this disclosure and the reproductions are performed in a pattern or in a way that such the body recognizes the reproductions as action potentials, wherein in U.S. Pat. Nos. 5,107,835 and 5,109,848, which was published in 1992 or U.S. Patent Application No. 20130060304, the application of the electrical direct current resulted in only incidental matching of the frequencies with the natural action potentials. In contrast, the current invention individualizes the action potential and fully utilizes the natural action potential by creating an electronic version of it that the body recognizes as a real action potential. This in and of itself is an invention. A further invention is the ability to perform movements wherein there is a higher level of "matching" or recreating a neuronal response is made when the changing frequencies match the changing frequencies of the muscle in question (wherein scientifically it is understood that the brain believes this movement is associated with multiplied reproductions of the action potential). Although normally this pattern was not achievable in prior art because the inability of the direct current electrical currents to penetrate the outer body and outer epidermis of the body, the current invention allows such capabilities by using two frequencies—one to sync with the body and another to pulse and mimic the nerve action potential.

This is distinguishable from prior art in that prior understanding of the so-called "weakened" muscle were due to the misunderstood concepts in muscle recovery. The current invention accepts the natural dynamics of the action potential and uses the ability of each individual to engage with a reproduction of the action potential, and more importantly, the current invention allows the ability to standardize the form of defining the level of efficiency based on this understanding and also allows for a higher level of recovery from isolating the muscles and parameters that allow for the highest match between an individual subject (whether animal or human) and a reproduction of pulsed electrical currents specifically aimed at mimicking its respective action potential so that the brain can re-engage and re-activate the muscle.

Currently, there is no way of accurately stating the muscle status other than to say "the muscle is weak" or the "muscle is not working" or "muscle is not contracting." By using the methods in this disclosure, a technician will be able to provide a numerical or grade value to the level of muscle inefficiency. Table 2 provides the permutations of ways to derive that numerical value. For example, the heart rate can be measured during stimulation of electrodes 907, 908, 909, 910, and 911, and these measurements may be made over some period of time over different areas of the muscles, and if analogous heart rates were measured in a previous session or on the other side of the body or exist in database of standards, there can be a ratio on which to base a numerical value. In this case, let's say that the pain threshold at electrode 910 occurs at 50 mA of current, when on the exact opposite side of the arm the same threshold occurs at 100 mA. A ratio of the difference (50) to the highest level (100) can determine the level of inefficiency in that muscle. A technician can say that the muscle inefficiency ratio is 0.5 (or 5011 00) which can provide an actual, precise number of 0.5. This threshold can be determined by either subjective or objective input, such as discomfort level from a scale of 1 to 10 or the average rise of heart rates in a given longer period of time.

In the expired U.S. Pat. No. 5,107,835, very specific forms of multiple wave patterns are used, but the current invention shows higher, even unexpectedly high results, when the waveforms are individualized and there is a manner to mimic the action potential. The application of frequencies in the expired patent may show success in re-engaging the brain, but these are incidental considering the frequency of the actual action potential does not exactly match with the frequency naturally occurring. That is because the frequency that is naturally occurring is slightly changing depending on the constant communication between the brain and the muscle. The current invention shows how one can derive at that frequency and if not exactly, enough so that performing certain movements can actually provide the stage by which the application of varied frequency used in the machine and with constant feedback from the client can result in a match between the real action potential frequency and the body. More importantly, when this is achievable, one can measure it and use it as a standard to determine overall muscle efficiency. More importantly, because the isolation of the frequency and waveform provides individualized care, those frequencies can be turned on high (current) and with the same amplitude and regression pattern and the mimicking of the action potential frequencies, the results in re-engaging the muscles have been unexpectedly high.

Current technology including U.S. Pat. No. 5,107,835 does use varied frequencies to engage the muscles, but those pulses overload the neurons to force the action potential, and they do not mimic them. By changing the pattern of waveform delivery and then creating a baseline from which the pulses can be varied in periods (or frequencies) as shown in FIG. 14, the body suddenly syncs with the action potential when matched. Studies in over 50 subjects showed greater than 35% improvement of muscle efficiency when these particularized wavelengths and frequencies were matched with action potentials. Even higher results were shown when these varied frequencies were increased at a constant rate during the contraction of the muscle. More than 40% improvement was shown in patients when movement of contracted muscles were combined with the varied frequencies of the delivery of reproduced action potentials. Even higher results were shown when the movements were performed to an accelerated level such that failure of the muscle came at an accelerated pace; and when this was matched with accelerated increases in frequencies in conjunction with the time. For example, the increase in frequencies was varied by 150 mV from beginning to end. The reproduction of the action potentials were given in the multiple frequency format as described in this disclosure. The patient contracted the muscles where the electrodes were placed from 0 seconds to 3 minutes. During this 3 minutes, the patient went from 0% effort to 100% effort until the muscles went to completion and failure. During this same 3 minutes, the application of the frequencies was increased from the low end to over an increase of 150 mV in the 180 seconds proportionally and in accelerated form. Both resulted in over 20% improvement in muscle efficiency based on heart rate variability measures.

The creation of a national database in contemplated within the particular example and within the context of Table 2, Criteria factor "database standards." The efficiency standards for each animal may differ. And each muscle will differ in muscle efficiency standards. Each muscle is different size and has a different purpose. The frequency set for each neuron and its connection to that muscle is particularized. Although the muscles on the left side of the body can be compared to the right side (a basis for one of the standards in this disclosure) and although the muscles can be compared individuals based on agonist/antagonist and from previous sessions (a history that defines a baseline of normal muscle efficiency), the difference between each individual and each animal and each muscle group is varied by the difference in the frequency that is needed for that muscle. Considering this variety, national standards for human and for animals would be necessary for the creation of standards on what would be "efficient" and what would be "inefficient" and what value of inefficiency that can be placed on the muscle. For example, the frequency for a human bicep is at 80 hz for the second electrical wave pulses. This is based on the standards of a human and over 500 patients studied as to what frequency triggered the highest heartrate variability increase. For the dog, the bicep is at 70 hz for the second electrical wave. The exact reasons are unknown as to why the differences occur, but there is consistency to show a range or a consistent frequency for non-movement and movement based calculations. A national database can be controlled via standard Internet connections and there can be crowd-sourcing capabilities to pool data for creation of standard in the frequencies and techniques used with frequencies that best result in a match.

Figure 13:
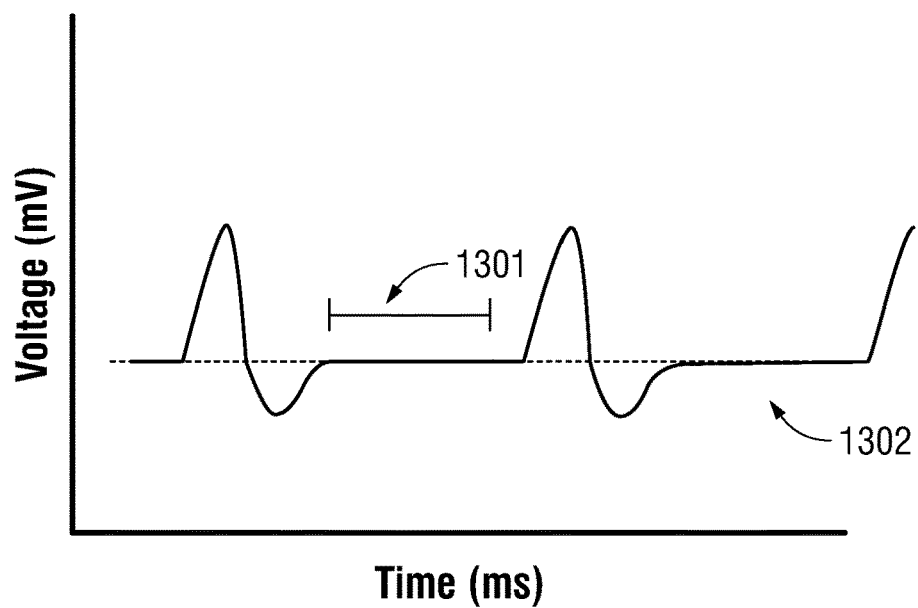
FIG. 13 shows an individualized wave pattern showing that the pulses can be varied until the body and brain recognizes each pulse as a natural action potential.

The best scientific understanding of this principle credits this success to the potential to better sync with the frequency of the natural pattern. For example, in throwing a dart, the triceps has to contract and the biceps must extend during the dart throw. FIG. 13 shows a waveform application in accordance with one embodiment of the current invention wherein the time between pulses (1301) is varied until each of the pulses is recognized as a natural action potential. This occurs differently in every individual, but the increase in discomfort or objective measures, like the heart rate, can indicate clearly the varied state at which the nerves resonate with the second set of frequency. As a result, individualized waveform patterns can be created and stored for future use. Having a matching resonating frequency has shown over 30% increase in muscle efficiency measures in over 500 patients tested.

By isolating the particular location of the muscle inefficiency as described above, and then applying specific currents, the waveform pulses can be increased in frequency (or duty cycle) section 1301. Section 1301 can be milliseconds in variation or it can be actually seconds. The pattern of 1302 must be repeatable so that the brain believe that each delivery of a pulse is a natural pulse—and in order to do that, the 1301 lengths are varied or increased until optimized. The variation can be involved in a diagnostic testing that shows which variation best syncs. At some point, the brain will believe that the signals are actually natural action potentials. Although U.S. Patent Application No. 20130060304 do carry traits of a peak and a regression pattern that is similar, the incidental application of these currents are not synced with the individual. In one particular example, Patient A used separation of these pulses and variations were tested. It was soon discovered through variation of heart rate measures that a further separation of the pulses was needed, and once pulse spacing was changed, Patient A was able to achieve higher levels of muscle efficiency rebridging when the power was increased at the same wavelengths. In other words, once the appropriate separation of the wavelength was discovered at a particular location of the muscle, the power current was increased using that same wavelength that mimics the action potential. When given in a tempo that is recognized by the natural body results are accelerated.

When paired with particular techniques of training and therapy, the application of these frequencies triggers a natural response in the brain to re-engage with the muscles to make them more efficient. As one example, a patient can perform a proper lunge movement, and with the application of the electrodes on very specific areas of the hamstring (located by the processes earlier described), the wavelength pulses can be varied until there is a response from the brain indicating that the second set of frequencies has reproduced an action potential voltage signal. When this signal is combined with the exercises, it re-engages the brain to make these muscles more efficient.

Ideally, in perfectly healthy muscles, there would be no heart rate increase or discomfort felt even at the maximum level of power applied to the most sensitive areas of the muscles. Since such elite levels are very difficult to obtain, there is a need to create a standardized system based on the individuals that can track progress towards this ideal.

Individuals carry different weight, water content, and different levels of fat. Different levels of electrolytes in the body also affect the levels of intensity from the stimulation treatments. However, consistent use of the treatments on one individual can provide valuable data, such that if an initial diagnostic is done, later on treatments can be compared to the initial diagnostic baselines so that a ratio of inefficiency can be made in accordance to the criteria of Table 2. Individuals tend to show a consistent pattern from previous sessions, and deviations from that pattern can provide meaningful insight into which variables are affecting their situation.

Example 4

Patient A performs a diagnostic wherein the biceps and the triceps are measured. Patient A achieves a maximum output power of 67 on a machine that has power settings ranging from 0 to 100 wherein 1 is the lowest setting and, proportionally, 100 is the highest setting, which can be a current as high as 200 milliamps. Patient B achieves a maximum of 59. Both of these points are reached by an objective test as described in Table 2, and in this case, the threshold occurs when the heart rate increases by 30%. In other words, patient A's heart rate increased 30% when the setting was set to 67 for more than 1 minute. In Patient B, that 30% increase happens at a setting of 59. Two weeks later, the same measurements are made. Patient A was able reach a level of 74, indicating an improvement in efficiency, either as a response to the previous test stimulation or something else that affected Patient A in the interim period. Patient B dropped to 43, and upon investigation, it was found that he had suffered an arm injury which made his triceps inefficient. Over 4 weeks, both Patients A and B were able to reach higher levels, and using their initial 67 and 59 as the baseline, a ratio of improvements can be determined. Patient A achieved a consistent 84 after 4 weeks, or had an efficiency improvement of 84/67, which is a 1.254 index of improvement. Patient B eventually reached a level of 61, even after the initial drop due to injury, which is 61/59, or a 1.034 index of improvement (the index would be even higher, of course, if calculated from the lower interim value of 43). Patient A was able to start at a higher efficiency state, and was also able to make a greater improvement over his own numbers based on the 1.254 index in comparison to Patient B's 1.034 index. In this case, the higher index means greater increases in muscle efficiency. There can also be ratios that compare a patient's inefficient muscles to the most efficient muscles in that same patient's body, so that every muscle can have its own index of relative inefficiency and know how much it needs to "catch up" to work at the same level as its counterparts. In other words, if Patient A's quadriceps could reach 100, then the bicep's efficiency is now 84% based on the Maximum Intra-Individual achievable standards. This is an easy way to translate a condition of a muscle to a different user, either on an absolute scale or on an individualized scale for each user.

By utilizing the action potential trigger of the body, various training techniques have been found that when used in conjunction with the frequencies produce even a higher rate of improvement in making the muscles efficient. Compared to prior art, we have shown that there is unrealized potential using a design that more closely mimics the voltage action potential occurring in the natural setting. Instead of just putting an injured knee in a cast or brace, this invention can dramatically accelerate the healing process for an injury. Performing a diagnostic procedure to precisely find the individual's necessary electrode placements and individualized wavelength parameters, and creating an index to prioritize the greatest muscle inefficiencies, can guide stimulation treatments. Such a process, which is essentially an algorithm, will determine where and how to stimulate the patient to achieve the greatest acceleration in healing and fastest return to function. Because of the standardization of the muscle efficiency, a new way of implementing computer technology can be used in the application of the frequencies. Currently, there are only vague and often scientifically inaccurate discussions of why techniques involving proper placement of the electrodes and use of direct current can improve muscle efficiency. The current invention allows the ability to describe the muscle inefficiency in a manner that is quantitative, and with that capability, it allows the understanding that the neuronal-muscular bridging is done best when the action potential of a neuron is mimicked.

There is hardly any research available regarding the efficiency changes to the muscles. When combined with specific exercises or movements, the pulses bridge the brain's connection to the working muscles so that they become more efficient even when the machine is no longer being applied. This is because of the application of the pulses, whether it be from two or three or more electrical currents, allows the brain to recognize patterns. This process allows the muscle to perform at a higher level, and in many cases it strengthens the muscles at rates faster than what can be achieved with merely lifting weights.

For example, during the action of throwing a dart, the muscles of the biceps 1405 and triceps 1406 work in combination to produce the natural power to extend the arm. The biceps must extend and the triceps must contract in a coordinated manner. If one set of muscles is less developed than the other, it often results in the inability of the less efficient muscles to extend properly, which eventually leads to injuries of the joints, such as tendinitis. Studies have shown that the application of dual frequency electrical currents that are synced with the actual movement of the arm can aid in the recovery of lost muscle efficiency. For example, if a dart thrower has underdeveloped triceps, then the triceps contraction will be insufficient to promote the actual extension of its opposing muscle, the biceps. By attaching electrodes to the triceps and timing the exercises such that the current is applied during the extension of arm in the throwing movement, the triceps are regulated to contract more efficiently.

Example 5

To do this, there is conceived different phase settings of the application of the multiple electrical currents. Phase A settings would promote concentric, overcoming, or positive contraction, and assist muscles on the lifting phase of a movement. This is done by altering the power of the second set of electrical current or by altering its frequency to harmonize with the action potential signals that trigger muscle contraction. Conventional microprocessors can be programmed to apply the proper Phase A settings during this phase of a movement. This phase switching can also be triggered by a mechanical device. For example, a sling on an arm that recognizes the extension of the arm can be attached such depending on the extension of the arm, the application of Phase A is delivered to the patient. Because the action potential of individual clients varies (especially if other animals are being used as subjects), the technicians applying the electrical currents must have the ability to slightly alter the wave's amplitudes and frequency (not in shape of waveform).

Phase B settings would be programmed to promote eccentric, yielding, lengthening, negative contraction, and assist muscles on the lowering phase. This is done by varying the flow of current, again changing the amplitudes and frequency to promote the opposite type of contraction. A mechanical device can also trigger the switching from Phase A to Phase B, such that the machine will work differently to promote different types of muscular contraction.

With experience, research has uncovered a surprising result that when the direction of these sound waves are applied in reverse polarity in comparison to the contracting or releasing form of exercise, the ability to re-engage and bridge the brain to make these attached muscles much more efficient allowing these muscles to regain their ability to properly absorb force. The polarity of the flow can also be matched with the eccentric, yielding, lengthening, negative contraction such that one way can be designed to the contraction of the muscle, and the other polarity is set on the release of the muscle. This reversal is particularly valuable when the electrodes are placed on opposing sets of muscles, so that the current can be directed towards one set for half of a bodily movement, and changed to be directed towards the opposite set for the other half of a movement. According to clinical evidence, it is shown that such matching of variables, such as the polarity and power, during particular exercises results in over 50% higher levels of brain connectivity and muscle stimulation.

In another embodiment of the invention, settings for Phase A and B can be matched with muscle efficiency numbers and show precise locations of muscle inactivity. The output can also be alternated between Phases A and B at preset timed settings, such as a setting that automatically alternates between Phases A and B at pre-set intervals, i.e. 5 seconds lower/5 seconds raising, 10 seconds lowering/1 second raising, 60 second lowering/60 seconds raising, etc.

Phases A and B are determined by the combination of frequencies and amplitudes that best promote each type of contraction. And because these levels actually vary by individual, it is necessary for the ability of the technician to store the client data of baseline levels so that the technician can identify progress or have the ability to spot inefficiencies of muscles.

Phase A and Phase B are different for individual users and are different for muscles that are being targeted. Thus, according to another embodiment of the invention, there is disclosed a means to store different settings and parameters including power, frequency, amplitude and waveform of different muscle groups. Conventional LCD screens can display "Quads" or "Pectorals" or "Biceps" according to the targeted muscles. The method includes a system that recalls the various settings for each of the targeted muscles. For example, for the Quads, the method includes frequency, amplitude, power, and waveform parameters that best results in a determination of muscle inefficiency, which can be measured by subjective determination of patients or objective factors, such as heart rate or heart rate variations over a certain time period, such as a minute. The method also includes the ability to recall those stored settings for later use. The method also allows for the baseline of treatments be changed depending on initial diagnostic test of individuals because of the variations that exist between individuals.

The underlying mechanisms explaining why these techniques work better and more efficiently are only now in 2015 being researched. Science suggests that the natural firing of these action potentials that occurs in these contracted and extended positions is enhanced when the external stimulation is timed precisely with the bodily movements. These studies are not just anecdotal, but show real objective improvements in performance.

With research, it is now understood that, in most people, concentric contractions are best promoted by lower frequencies and higher amplitudes, while eccentric contraction is best promoted by higher frequencies and low-mid-range amplitudes. This typical pattern can vary per person based on the degree of their training and neurological development. Because the settings are different in each individual, research has also developed techniques to establish a baseline for each individual by performing a set of diagnostic tests that informs the technician and the machines what initial settings are required and what forms of timed interval settings are best for each exercise.

Example 6

Figure 15A:
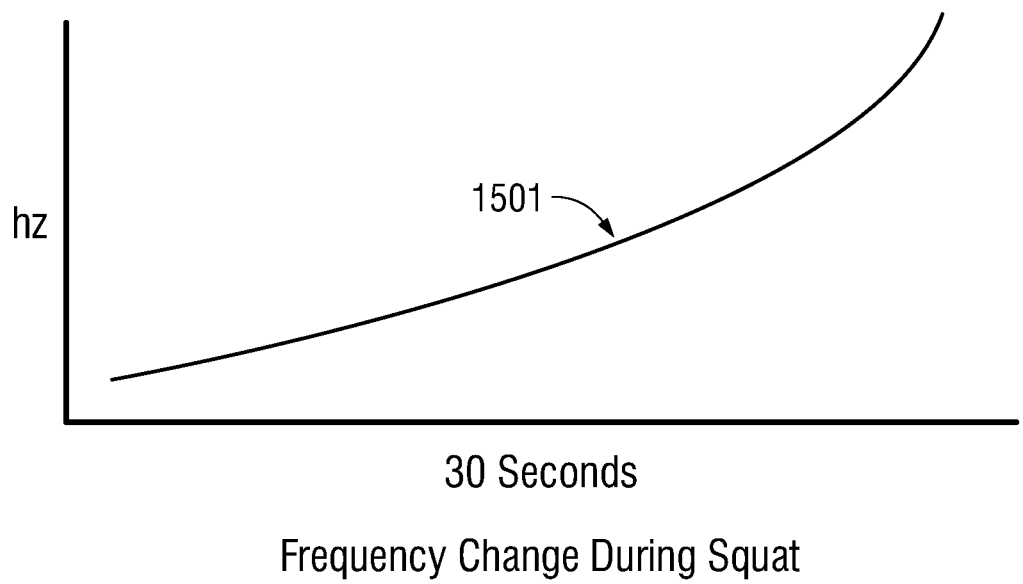
FIG. 15A shows a normal frequency change of an action potential during a 30 second squat exercise.
Figure 15B:
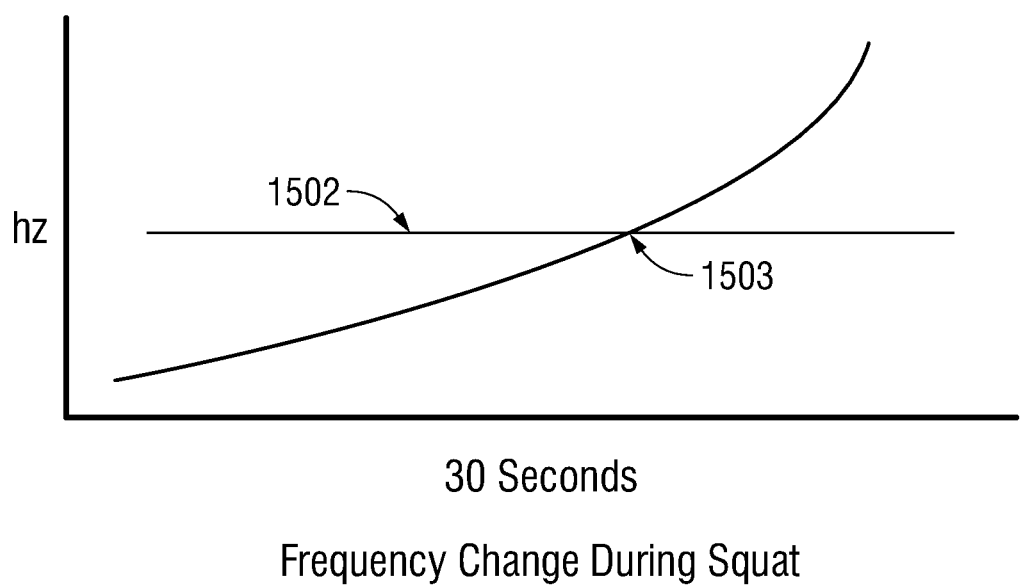
FIG. 15B shows additionally an addition of a static frequency that is known in the prior art.
Figure 15C:
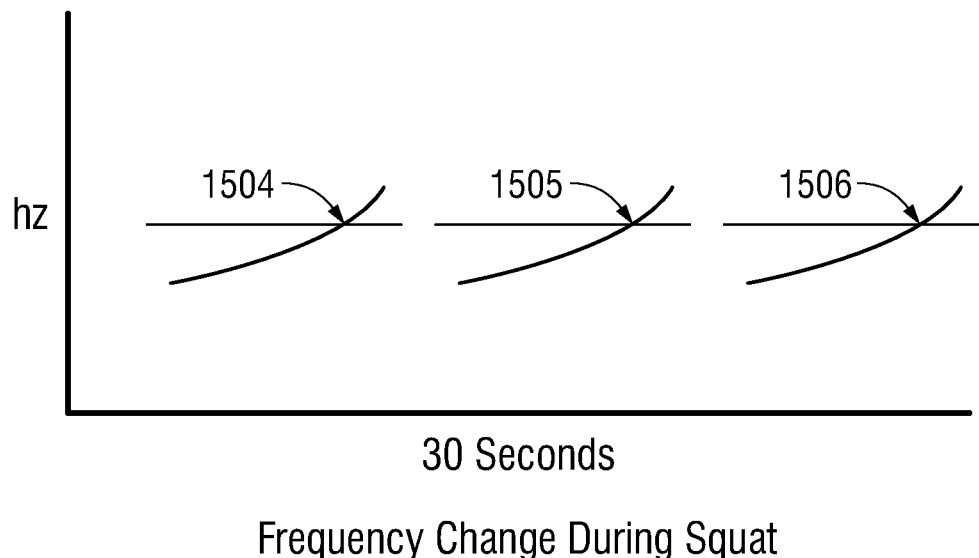
FIG. 15C shows additionally a representation of how on/off switch can intersect with the proper frequency more often than once.
Figure 15D:
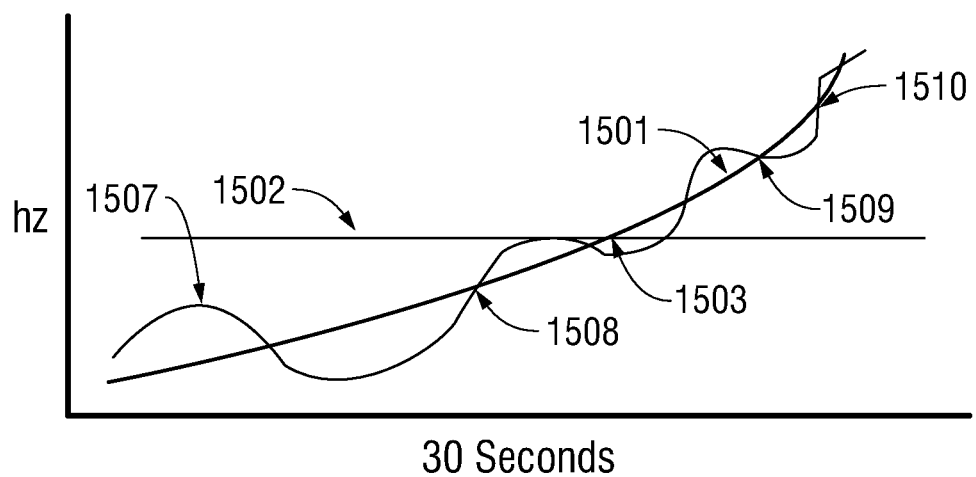
FIG. 15D shows an embodiment of the current invention that tries to match the proper frequency and the frequency changes with the natural frequency changes that results in higher yields of making muscle more efficient.

The goal is the match the natural action potential produced by the body with the reproduced action potentials by predicting that the natural action potential will exponentially increase, and thereby increasing the reproduced action potential exponentially. During a long squat exercise over a period of 30 seconds, if the frequency of the second pulsed electrical current is matched to the natural action potential, significant improvement in muscle efficiency is found by over 15% compared to controls. The method involves varying the frequency over a longer period during a diagnostic stage wherein a match is made. A match is made when there is an increase in the parameters (discussed above, such as heart rate variability, blood pressure, breathing, perspiration and subjective input) to an exercise that especially contracts that muscle. FIG. 15A shows how the frequency in a normal squat exercise can alter during a 30 second squat in healthy patient. Line 1501 is curved upwards in an exponential way such that the needed frequency at higher rates of the exercise is needed. FIG. 15B shows how sending a "prior art" direct current pulse 1502 that is constant can incidentally hit the natural curve at 1503. FIG. 15C is a representation of what turning the machine on and off can do—by turning the on/off switch the incidental hits can actually occur more frequently, and thus by performing certain exercises at certain frequencies and changing them can mimic the natural action potential more closely rather than sending an uncharacteristically similar frequency. Intersections at 1504, 1505, and 1506 shows how carrying the on/off switch can produce interactions that coincide more frequently with the natural action potential than in 15B. FIG. 15D involves a diagnostic testing of the patient such that feedback results in isolating the frequency pattern, and once the frequency pattern is stored, it can be reproduced during the squat exercises, and as shown in the intersections of 1508, 1509, and 1510, the frequency can be narrowed with the feedback such that during exercises, a match can be made of the reproduced frequency and the natural frequency as shown in 1507 pathway. Such ability to mimic the natural action potential has yield in higher rates of muscle efficiency which has resulted in faster recover rates from injuries and faster development of muscles in training.

Example 7 utilizes design custom circuit and firmware to control electrical output of both dual signals and to control the environment in the soundwave frequencies. The use of multiple frequencies wherein one of the frequencies is a carrier wave that allows the second electrical current to penetrate and reach desired nerves is performed using conventional machines that can vary the frequencies, as discussed throughout this disclosure and are contemplated in prior art machines, such as U.S. Pat. Nos. 5,107,835 and 5,109,848 machines. But these machines do not contemplate the use of precise waveforms that mimic more closely natural waveforms, nor do they utilize components with low noise using precise components for delivery of sound waves.

The music industry is filled with precise sound equipment made to reduce noise, and although it is unconventional to use sound equipment for neuromuscular stimulation devices, the development of neuromuscular stimulation devices using music internal components, such as transformers made for lower 0 to 1000 hz frequencies allows for a cleaner signal with a reduction of noise, which is vital in devices aimed precisely to stimulate muscle contractions.

Figure 17:
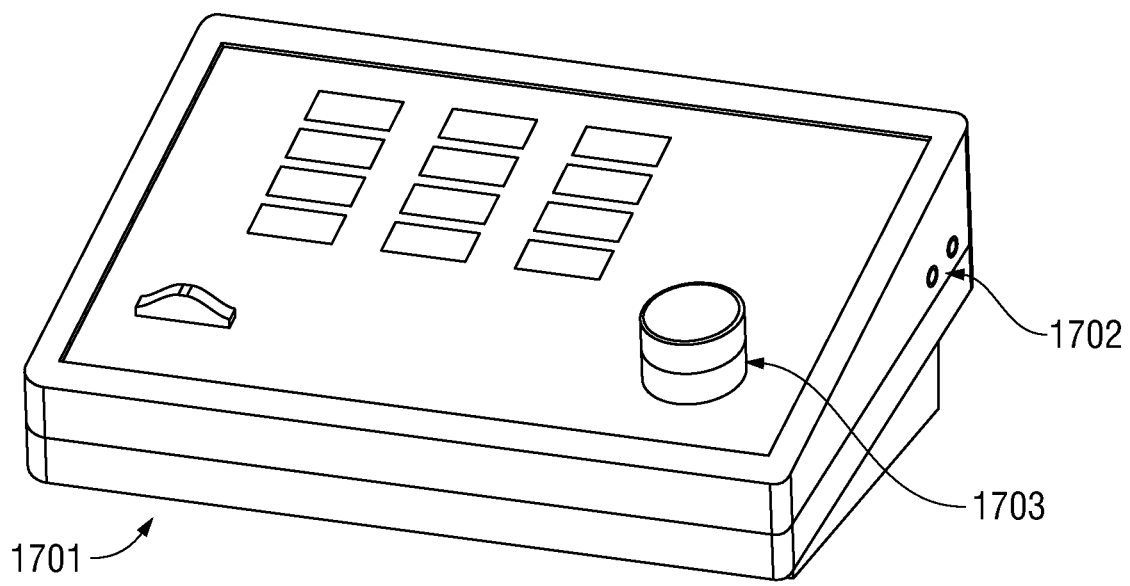
FIG. 17 shows the outer box of the Neubie, that discloses the system of the enclosed invention.

The system 1701 is powered using standard 120V 60 Hz AC power via an external wall-wart power supply or internal AC-to-DC conversion. (not pictured) The device 1701 pictured in FIG. 17 will have a master shut-off switch 1702 and will be modular in that each channel will be controlled individually through panel-mount controls. Channel outputs are the sum of two waveforms, a high and low frequency, with the output being capped at a pre-determined maximum value. A digital processor synthesizes the waveforms for output and will pass the results through digital-to-analog conversion and amplification stages. The output amplitude cap performs on the processor, and will also be clamped by hardware for redundancy. Firmware was developed using development environments MPLAB X and Microchip in parallel with the sourcing of the assembled circuit boards.

Figure 18:
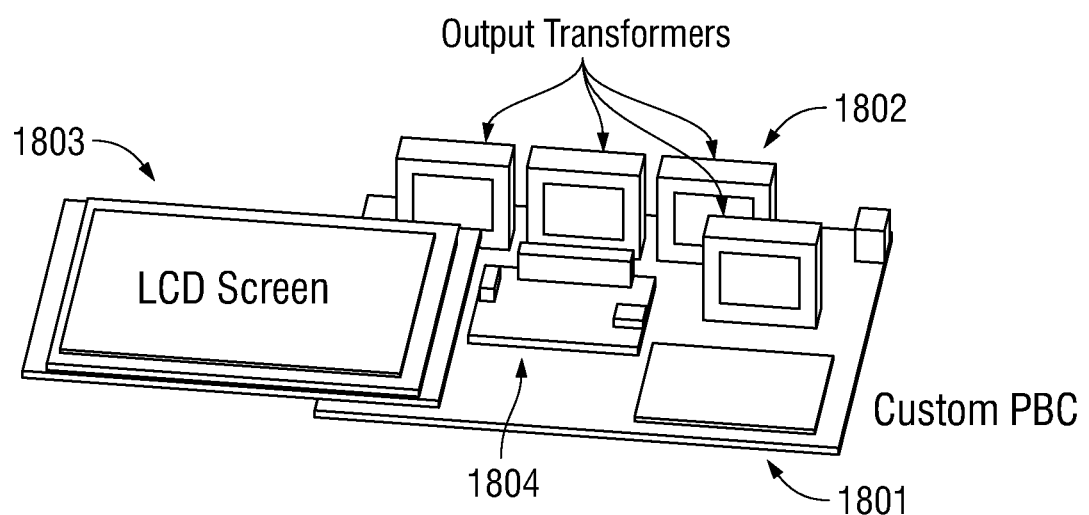
FIG. 18 shows the internal components of the Neubie, which discloses musical components geared to produce clean frequencies in the frequency range of 0 to 1000 hz.
Figure 19:
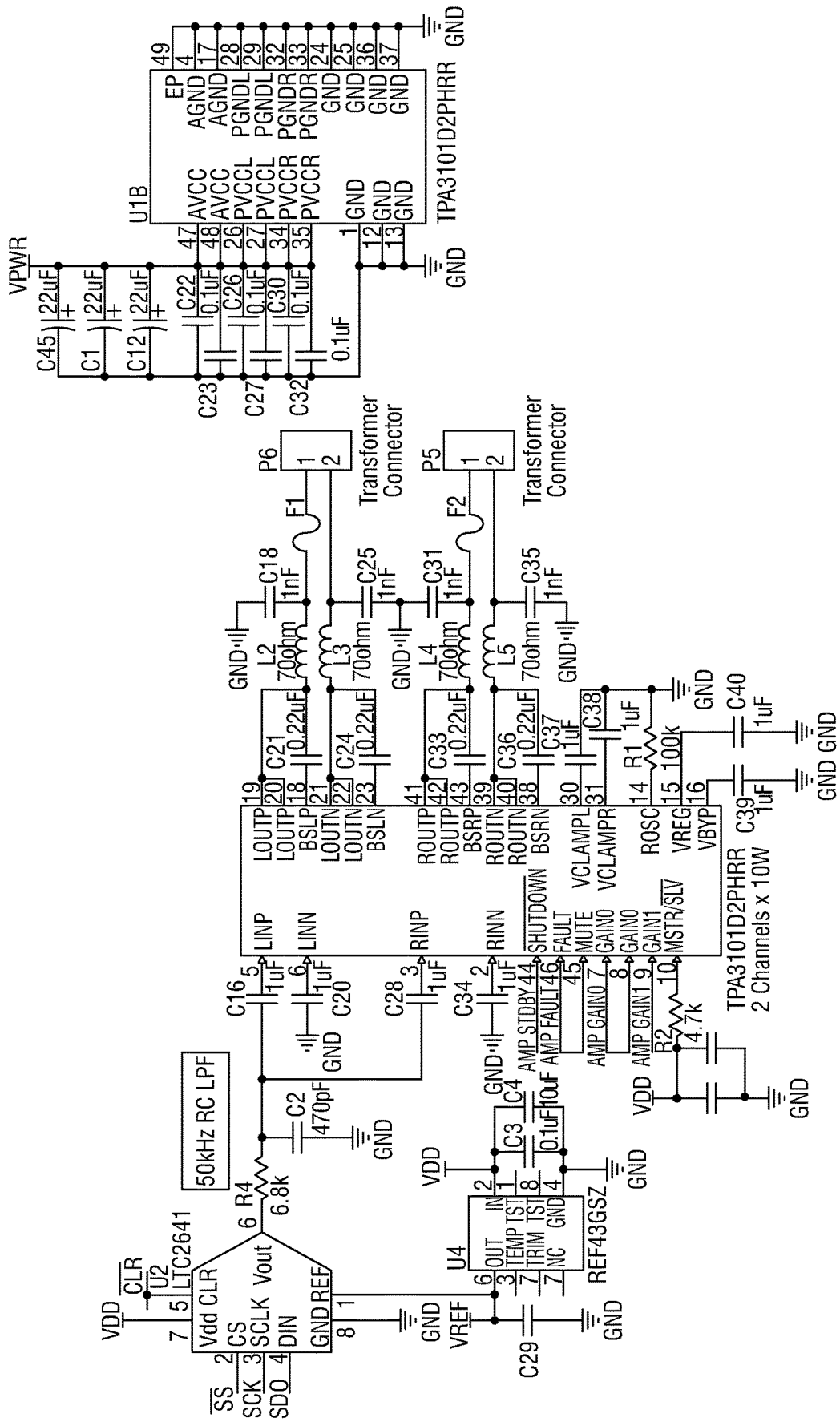
FIG. 19 shows the circuit board drawing of the electrode components that is capable of producing the multiple currents needed to disclose the system and methods of the current inventions.

A breadboard circuit was designed that utilizes digital waveform synthesis for creation of the stimulation waveform. The power stage consists of an audio amplifier driving output transformers 1802 in FIG. 18 which isolates the user electrodes from the digital electronics, earth ground, and input power. This stimulation topology offers a wide range of possibilities regarding waveform shape, input power requirements, and output power levels, lending to efficient design of instruments meeting varying application requirements. For example, waveform shape can be changed in firmware by simply reprogramming the device. Output power can be adjusted by either scaling the amplitude of the synthesized waveform, or by reducing the amplification of the audio amplifier. A preliminary circuit schematic is shown in FIG. 19. The schematic drawing illustrates the design of the waveform output stages. A microcontroller (not depicted) would control the LTC2641 Digital-to-Analog Converter (DAC) using the Serial Peripheral Interface (SPI) bus standard. The waveform created by the DAC passes through a low-pass RC filter and is then A/C coupled into both input channels of a stereo audio amplifier. Amplifier output, gain, and fault conditions are controlled and monitored by the microcontroller. The output of each audio amplifier channel passes through an EMI filter and a fuse before being connected to one side of the output transformer through connectors P5 and P6. Electrodes are connected to the opposite side of the output 1702 that are connected to the transformers 1802.

It is known to use load analogous to the human body—such as a simple RC circuit as described in U.S. Pat. No. 5,109,848. LCD screen and corresponding LCD internal component 1803 can be programmed to offer various pictures of electrode placements on the bodies or videos of various exercise movements that correspond with various exercises and routines consistent with descriptions in this disclosure.

The timing can be varied as the exercises can vary. There are variances in ways to compare the exercise and the contraction of the muscles with the needed frequencies, but because individuals are all different, it is best to create an individual baseline at each session or during previous sessions. Conventional machines that can vary the frequencies are contemplated in prior art machines, such as U.S. Pat. Nos. 5,107,835 and 5,109,848 machines, but these machines do not contemplate the harmonizing of the second set of direct currents with the action potential, and standardizing efficiency model based on objective/subjective measures of matching a variance of a reproduced action potential with the real action potential during precise movements that involves the use of those muscles.

Clinical studies and patient data have shown significant muscle efficiency improvements that have led to the treatment and proper healing in over 90% of the cases for the following injuries:
- Disc bulges, herniations of the cervical and lumbar spine
- Rotator cuff sprains, strains, and tears
- Elbow tendon and ligament injuries, including tennis elbow, golfer's elbow, and
- UCL tears (the injury for which Tommy John surgery is often required)
- Sacroiliac Joint Dysfunction
- Pain from Degenerative Joint Disease in the Hip and Knee
- Strained/Torn Muscles
- Non-surgical rehabilitation of torn knee meniscus
- Ankle Sprains/Strains/Tears
- Plantar Fasciitis Further, the training that involves the more efficient use of muscles by using various electrodes that trigger activation of the body's reduced muscles has proven to improve muscle mass, strength, flexibility, speed, and endurance in many different sports, including the successful training of athletes in the following fields:
- Football, Baseball/Softball, Basketball, Soccer, Hockey, Volleyball, Swimming
- Track and Field
- Dance—Ballet, Modern Dance, Competitive Cheerleading
- Powerlifting and Olympic Lifting
- Bodybuilding
- Car/Motorcycle Racing
- Wrestling, Martial Arts
- Gymnastics and Diving
- The so-called "Extreme Sports" like Skateboard, Motocross, Wakeboarding, etc.
- Mountain Climbing and Rock Climbing Because enhancing muscle efficiency can enhance the performance of muscles, increased muscle efficiency has led to clinically validated improvements in performance for participants in many activities and sports. For example, let's take the common bench press. Traditional bench pressing typically only strengthens the pressing muscles, like the pectorals, front deltoids, and triceps. An overlooked key to this movement is actually the pulling muscles, those of the upper back and biceps. When they work correctly, these muscles can pull the pressing muscles into proper position so that they are lengthened out, loaded like a bow and arrow. This is important, because these lengthened muscle can absorb much more force to protect the shoulder and elbow joints. When properly lengthened, they will also produce much more force and allow more weight to be lifted in the pressing phase. The present invention can be applied to facilitate both the lengthening of the pressing muscles, and also the ability of the pulling muscles to pull into the correct position to promote that lengthening.

In another embodiment of the invention there is another form of determining muscle efficiency by determining the locations of a muscle that experience the least efficient connection to the brain and thus are reduced in efficiency. The method may involve applying sound wave frequency electrical currents in a location A of a muscle and then identifying a location on a precise location of a muscle where there is associated a certain level of discomfort and then relocating the application of sound wave frequency currents to a location B and then comparing the discomfort from location A to location B and determining whether location A or location B was higher. Further a larger number of locations can be labeled, which may be XY axis of a particular muscle or in small or odd shaped muscles, each muscle only needs a consistent manner to label and show patients the level and degree of inefficiency. By creating different locations with varying degrees of response from the currents, a map can be made (like a topographic map) showing more specifically the location of the inefficiency in muscle that is being targeted.

A further embodiment of the invention involves the use of these electrical currents to be applied specifically during muscle extension exercises. In this example, a stretch position, like a lunge position involves the use of the quads, hamstrings, hip flexors, and gluteal muscles. When the muscles in the back leg are fully extended, the quads and hip flexors must eccentrically contract to absorb force and protect the knee, hip, and lower back. Applying the present invention enhances the ability of the brain to control these lengthened muscles, which then allows the body to be more stable at greater ranges of motion. The result is improved flexibility in way that is safer than traditional stretching, because in this method the muscles are lengthened and can absorb force rather than bracing against the support of ligaments and other connective tissue as happens in traditional stretching.

While an example of suitable hardware is provided above, the invention is not limited to being implemented in any particular type of hardware.

Further, it should be recognized that embodiments of the present invention can be implemented via computer hardware or software, or a combination of both. The methods can be implemented in computer programs using standard programming techniques—including a computer-readable storage medium configured with a computer program, where the storage medium so configured causes a computer to operate in a specific and predefined manner-according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

Further, throughout the present specification, discussions utilizing terms such as "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

The invention has broad applicability and can provide many benefits as described and shown in the examples above. The embodiments will vary greatly depending upon the specific application, and not every embodiment will provide all of the benefits and meet all of the objectives that are achievable by the invention.

Further, whenever the terms "automatic," "automated," or similar terms are used herein, those terms will be understood to include manual initiation of the automatic or automated process or step.

In the following discussion and in the claims, the terms "including" and "comprising" are used in an open-ended fashion, and thus should be interpreted to mean "including, but not limited to . . . ." The term "integrated circuit" refers to a set of electronic components and their interconnections (internal electrical circuit elements, collectively) that are patterned on the surface of a microchip.

To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions, and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of enhancing muscle efficiency in a muscle comprising:
applying a first set of current pulses, via a neuromuscular stimulator, that are pulsed at a first set pulse rate between 20 pulses per second (pps) and 20,000 pps to a target muscle, wherein the first set of current pulses acts as a carrier frequency;
applying a second set of current pulses in combination with the first set of current pulses to the target muscle, wherein the second set of current pulses have an amplitude and a second set pulse rate between 1 pps and 1000 pps, wherein the second set of current pulses acts as a stimulation frequency; and
setting the pulse rate of the second set of current pulses to a first level to stimulate the target muscle contractions during performance of a lengthening movement occurring during an interval training exercise, wherein the stimulation during lengthening movement for the target muscle eccentric elongation is configured to (a) increase work of the muscle during the lengthening movement, (b) stimulate sensory receptors sensing changes in muscle length, and (c) increase tissue load for training in order to accommodate the changes efficiently.

2. The method of claim 1 wherein the first level pulse rate of the second set of current pulses applied during the lengthening phase of the movement to lengthen the target muscles and to promote eccentric elongation of muscles is an increased pulse rate relative to the pulse rate of the second set of current pulses administered during other parts of the interval training exercise.

3. The method of claim 1, wherein the first level pulse rate frequency of the second set of current pulses is greater during the movement to lengthen the target muscles to promote eccentric elongation of muscles during lengthening than a second level pulse rate of the second set of current pulses during movement and is configured to promote concentric shortening of muscles in the opposite shortening phase of the movement.

4. The method of claim 1, further comprising:
adjusting the pulse rate of the second set of current pulses to a second level decreased from the first level during performance of shortening movement during the interval training exercise to promote concentric shortening of muscles in the opposite shortening phase of the movement.

5. The method of claim 1, further comprising:
measuring a level of work performed by the target muscle in a first instance with measurements of at least one of a maximum heart rate, heart rate variability, average heart rate, blood pressure measurements, oxygen saturation level measurements, breathing rate, or galvanic skin response measurements of perspiration level in a patient; and
measuring a level of work performed by the target muscle by increasing the voltage of the first and second set of current pulses applied on the target muscle in a second instance and comparing with corresponding measurements of at least one of a maximum heart rate, heart rate variability, average heart rate, blood pressure measurements, oxygen saturation level measurements, breathing rate, or galvanic skin response measurements of perspiration level in a patient performing the lengthening movement.

6. The method of claim 1 wherein the first level pulse rate of the second set of current pulses applied during the lengthening phase of the movement to lengthen the target muscles is in a range above 100 pps and a second level pulse rate of the second set of current pulses is in a range of 20-80 pps during the movement to promote concentric shortening of muscles in the opposite shortening phase of the movement.

7. The method of claim 1 wherein the delivery of first set of current pulses and second set of current pulses during application to contract the target muscles is done using a first set of electrodes on a target muscle.

8. The method of claim 7, further comprising:
applying to an opposing muscle opposite to the target muscle, via a second set of electrodes, a third set of current pulses at the carrier frequency and a fourth set of current pulses at a second level pulse rate lower than the first level pulse rate of the second set of current pulses applied to the target muscle.

9. A method of enhancing muscle efficiency in a muscle comprising:
applying a first set of current pulses, via a neuromuscular stimulator, that are pulsed at a first set pulse rate between 20 pulses per second (pps) and 20,000 pps to a target muscle, wherein the first set of current pulses acts as a carrier frequency;
applying a second set of current pulses in combination with the first set of current pulses to the target muscle, wherein the second set of current pulses have an amplitude and a second set pulse rate between 1 pps and 1000 pps, wherein the second set of current pulses acts as a stimulation frequency;
setting the second set pulse rate to a first level to stimulate the target muscle contractions during performance of a lengthening movement occurring during an exercise configured to (a) stimulate sensory receptors sensing changes in muscle length, and (b) increase tissue load during the lengthening movement for target muscle eccentric elongation to increase work of the muscle during the lengthening movement; and
adjusting the second set pulse rate to a second level during shortening movement of the target muscle to promote concentric shortening of muscles in the opposite shortening phase of the movement.

10. The method of claim 9, wherein the voltage of the second set of current pulses can be increased or decreased during the movement to increase resistance during eccentric elongation of muscles during the lengthening movement of the exercise.

11. The method of claim 9 wherein the delivery of first set of current pulses and second set of current pulses during application to contract the target muscles is done using a first set of electrodes.

12. The method of claim 9 wherein the second set pulse rate first level is a greater frequency than the second set pulse rate second level.

13. The method of claim 9 wherein the second set pulse rate first level is between 100-500 pps.

14. The method of claim 9 wherein the second set pulse rate second level is between 20-80 pps.

15. The method of claim 9 further comprising:
applying a third set of current pulses at the carrier frequency and a fourth set of current pulses at the second level pulse rate to an opposing muscle opposite to the target muscle during performance of lengthening movement of the target muscle eccentric elongation and the opposing muscle shortening movement.

16. A method of enhancing muscle efficiency in a muscle comprising:
  applying a first set of current pulses that are pulsed at a first set pulse rate between 20 pulses per second (pps) and 20,000 pps to a target muscle, wherein the first set of current pulses acts as a carrier frequency;
  applying a second set of current pulses in combination with the first set of current pulses to the target muscle, wherein the second set of current pulses have an amplitude and a second set pulse rate between 1 pps and 1000 pps, wherein the second set of current pulses acts as a stimulation frequency;
  setting the second set pulse rate frequency to a first level to stimulate the target muscle contraction during performance of a lengthening movement during an interval training exercise, wherein the stimulation during the lengthening movement for the target muscle eccentric elongation is configured to (a) increase work of the muscle during the lengthening, (b) stimulate sensory receptors sensing changes in muscle length, and (c) increase tissue load; and
  applying the second set pulse rate frequency at the first level configured to promote muscle recovery during a resting phase between intervals of the interval training exercise to stimulate sensory receptors sensing a rest phase, promote muscle relaxation during no changes in muscle length, and increases in tissue load.

17. The method of claim 16 wherein the voltage amplitude of the second set of current pulses is configured to be increased or decreased during the movement to increase resistance during eccentric elongation of muscles during the lengthening movement of the exercise.

18. The method of claim 16 wherein the second set pulse rate first level is between 100-500 pps.

19. The method of claim 16 further comprising:
  adjusting the second set pulse rate to a second level at a lower frequency than the first level during shortening movement of the target muscle to promote concentric shortening of muscles in the opposite shortening phase of the movement.

20. The method of claim 19 wherein the second set pulse rate second level is between 20-80 pps.

* * * * *